US006939533B2

(12) United States Patent
Contag et al.

(10) Patent No.: US 6,939,533 B2
(45) Date of Patent: *Sep. 6, 2005

(54) NON-INVASIVE LOCALIZATION OF A LIGHT-EMITTING CONJUGATE IN A MAMMAL

(75) Inventors: Pamela R. Contag, San Jose, CA (US); Christopher H. Contag, San Jose, CA (US); David A. Benaron, Portola Valley, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 10/205,218

(22) Filed: Jul. 24, 2002

(65) Prior Publication Data

US 2003/0013132 A1 Jan. 16, 2003

Related U.S. Application Data

(60) Division of application No. 09/233,698, filed on Jan. 19, 1999, now Pat. No. 6,649,143, which is a continuation of application No. 08/602,396, filed on Feb. 16, 1996, now abandoned, which is a continuation-in-part of application No. 08/270,631, filed on Jul. 1, 1994, now Pat. No. 5,650,135.

(51) Int. Cl.[7] .............................................. A61B 10/00

(52) U.S. Cl. ...................... 424/9.6; 424/9.1; 424/9.61; 424/93.1; 424/93.2; 435/320.1; 435/325; 435/7.9; 435/368; 436/800

(58) Field of Search .................. 424/9.1, 9.6, 9.61, 424/93.1, 93.2; 435/320.1, 325, 7.9, 968; 436/800

(56) References Cited

U.S. PATENT DOCUMENTS

| | | |
|---|---|---|
| 4,178,917 A | 12/1979 | Shapiro |
| 4,341,223 A | 7/1982 | Lutz |
| 4,541,438 A | 9/1985 | Parker et al. |
| 4,762,701 A | 8/1988 | Horan et al. |
| 4,912,031 A | 3/1990 | Compton et al. |
| 5,171,749 A | 12/1992 | Levy et al. |
| 5,281,539 A | 1/1994 | Schramm |
| 5,283,179 A | 2/1994 | Wood |
| 5,332,567 A | 7/1994 | Goldenberg |
| 5,418,132 A | 5/1995 | Olivo |
| 5,435,307 A | 7/1995 | Friauf et al. |
| 5,466,575 A | 11/1995 | Cozzette et al. |
| 5,622,868 A | 4/1997 | Clarke et al. |
| 5,650,135 A | 7/1997 | Contag et al. |
| 5,683,888 A | 11/1997 | Campbell |
| 5,917,190 A | 6/1999 | Yodh et al. |
| 6,020,121 A | 2/2000 | Bao et al. |
| 6,217,847 B1 | 4/2001 | Contag et al. |

FOREIGN PATENT DOCUMENTS

| | | |
|---|---|---|
| WO | WO 86/01805 | 3/1986 |
| WO | WO 86/01806 | 3/1986 |
| WO | WO 91/01305 | 2/1991 |
| WO | WO 96/40979 A1 | 12/1996 |

OTHER PUBLICATIONS

Aizawa et al., "A New Diagnostic System for Malignant Tumors Using Hematoporhyrin Derivatives, Laser Photoradiation and a Spectroscope," *Porphyrin Localization and Treatment of Tumors* pp 227–238 (1984).

Alfano et al., "Fluorescence Spectra from Cancerous and Normal Human Breast and Lung Tissues," *Journal of Quantum Electronics* 23(10):1806–1811 (1987).

Alfano et al., "Light Sheds Light on Cancer–Distinguishing Malignant Tumors from Benign Tissues and Tumors," Bull N.Y. Acad. Med. 67(2):143–150 (1991).

Anderson–Engles, S. et al., "Fluorescence Imaging and Point Measurements of Tissue; Applications to the Demarcation of Malignant and Tumors and Atherosclerotic Lesions from Normal Tissue," *Photochemistry and Photobiology* 53(6):807–814 (1991).

Anderson–Engles, S. et al., "Laser–induced Fluorescence in Malignant and Normal Tissue of Rats Injected with Benzoporhyrin Derivative," *Photochemistry and Photobiology* 57(6):978–983 (1993).

Andrew et al., "Construction of Bioluminescent Mycobacterium and its Use for Assay of Antimycobacterial Agents," *J. Clin. Microbiol.* 31(9):2251–2254 (1993).

Araki, "Photo–detection of Transferred Gene Expression in Fish," *Chemical Abstracts 123*: Abstract No. 189418 (1995), abstract only.

Balchum, O. et al., "Imaging Fluorescence Bronchoscopy for Localizing Early Bronchial Cancer and Carcinoma in Situ," *Porphyrin Localization and Treatment of Tumors*, pp. 847–861, New York: Alan R. Liss Inc. (1984).

Ballou, B. et al., "Tumor Location and Drug Targeting Using a Monoclonal Antibody (anti–SSEA–1) and Antigen–Binding Fragments," *Journal of Surgical Oncology* 31:1–12 (1986).

Ballou, B. et al., "Tumor Labeling in Vivo Using Cy5–monoclonal Antibody," *Proceedings of the American Association for Cancer Research Annual Meeting* 35(0):504 (1994), abstract only.

(Continued)

*Primary Examiner*—Jennifer E. Graser
(74) *Attorney, Agent, or Firm*—Robins & Pasternak LLP

(57) ABSTRACT

Methods and compositions for detecting and localizing light originating from a mammal are disclosed. Also disclosed are methods for targeting light emission to selected regions, as well as for tracking entities within the mammal. In addition, animal models for disease states are disclosed, as are methods for localizing and tracking the progression of disease or a pathogen within the animal, and for screening putative therapeutic compounds effective to inhibit the disease or pathogen.

48 Claims, 23 Drawing Sheets

OTHER PUBLICATIONS

Baumgartner et al., "A Fluorescence Imaging Device for Endoscopic Detection of Early Stage Cancer– Instrumental and Experimental Studies," *Photochemistry and Photobiology:* 46(5):759–763 (1987).

Benaron et al., "A Medical Perspective at the Threshold of Clinical Optical Tomography," *SPIE Optical Engineering Press*, pp. 3–9 (1993).

Benaron and Stevenson, "Optical Time of Flight and Absorbance Imaging of Biologic Media," *Science* 259:1463–1466 (1993).

Benaron and Stevens, "Resolution of Near Infrared Time–of–Flight Brain Oxygenaton Imaging," *Oxygen Transport to Time XV, Edited by Vaupel et . Plemun Press, New York* 345:609–617 (1994).

Brodbeck et al., "A System for Real Time Fluorescence Imaging in Color for Tumor Diagnosis," *Med Phys* 14:637–639 (1984).

Bronstein et al., "Review Chemiluminescent and Bioluminescent Reporter Gene Assays." *Analytical Biochemistry* 219:169–181 (1994).

Casedi et al., "Expression and Secretion of Aequorin as a Chimeric Antibody by Means of a Mammalian Expression Vector," *Proc. Natl. Acad. Sci. USA* 87:2047–2051 (1990).

Chalfie et al., "Green Fluorescent Protein as a Marker for Gene Expression," *Science* 363:802–805 (1994).

Chance et al., "Photon Dynamics in Tissue Imaging," *Proc. SPIE* 1525:68–82 (1991).

Contag et al., "Optical Tracking of Infection in Vivo Using Light– Generating Probes," *Pediatric Research* 37:172a (1994).

Cubeddu, et al., "Time–Gated Fluorescence Imaging for the Diagnosis of Tumors in a Murine Model," *Photochemistry and Photobiology* 57(3): 480–485 (1993).

Cutler, M., "Transillumination as an Aid in the Diagnosis of Breast Lesions," *Gynecology and Obstetrics* 48(6); 721–729 (1929).

Fernández–Piñas, et al., "Expression of luxCD–E in Anabaena sp. Can Replace the Use of Exogenous Aldehyde for in vivo Localization of Transcription by lux AB," *Gene 150*: 169–174 (1994).

Folli et al., "Immunophotodiagnosis of Colon Carcinomas in Patients Injected with Fluoresceinated Chimeric Antibodies Against Carcinoembryonic Antigen," *Proc Natl Acas Sci* 89:7973–7977 (1992).

Folli et al., "Antibody–Indocyanin Conjugates for Immunophotodetection of Human Squamous Cell Carcinoma in Nude Mice," *Cancer Research* 54:2643–2649 (1994).

Frackman et al., "Cloning Organization and Expression of Bioluminescence Genes of *Xenorhabdus luminescens*," *Journal of Bacteriology* 172(10):5767–5773 (1990).

Francis et al., "Light Emission for a Mudlux Transcriptional Fusion in *Salmonella typhimurium* Is Stimulated by Hydrogen Peroxide and by Interaction with the Mouse Macrophage Cell Line J774.2," *Infection and Immunity* 61(2):640–649 (1993).

Gimble et al., "In Vitro and in Vivo Analysis of Murine Lipoprotein Lipase Gene Promoter: Tissue–specific Expression," *American Journal of Physiology* 268(2 Pt 1):E213–E218 (1995).

Goff et al., "Photoimmunotherapy and Biodistribution with an OC125–chlorin Immunoconjugate in an in vivo Murine Ovarian Cancer Model," *British Journal Cancer* 70:474–480 (1994).

Gould et al., "Firefly Luciferase as a Tool in Molecular and Cell Biology," *Analytical Biochemistry* 175:5–13 (1988).

Harats et al., "Targeting Gene Expression to the Vascular Wall in Transgenic Mice Using the Murine Proproendothelin–1 Promoter," *Journal of Clinical Investigation* 95(3): 1335–1344 (1995).

Hill et al., "Bioluminescence and Chemiluminescence Literature—Luciferase Reporter Genes—Lux and Luc", *Biolumin chemilumin* 8:267–281 (1993).

Hooper et al., "CCD Imaging of Luciferase Gene Expression in Single Mammalian Cells," *Journal of Bioluminescence and Chemiluminescence* 5:123–130 (1990).

Hooper et al., "Low–light Imaging Technology in the Life Sciences," *J. Biolumin Chemilumin* 9:113–122 (1994).

Horan et al., "Fluorescence Cell Labeling for in vivo and in vitro Cell Tracking," *Methods in Cell Biology* 33:469–490 (1990).

Jarry et al., "Imaging Mammalian Tissues and Organs Using Laser Collimated Transillumination," *Journal of Biomedical Engineering* 6:70–74 (1984).

Jassim et al., "In Vivo Bioluminescence: a Cellular Reporter for Research and Industry," *Journal of Bioluminescence and Chemiluminescence* 5:115–122 (1990).

Jöbsis, "Noninvasive Infrared Monitoring of Cerebral and Myocardial Oxygen Sufficiency and Circulatory Parameters," *Science* 198:1264–1267 (1977).

Kain et al., "Green Fluorescent Protein as a Reporter of Gene Expression and Protein Localization," *Biotechiques* 19:650–655 (1995).

Kaneko et al., "Fundamental Studies of Breast Tumor Detection with Narrow Beam Laser Scanning (Report 1)," *Radiation Medicine* 6(2):61–65 (1988).

Karp et al., "A Sensitive Model System for in vivo Monitoring of Baculovirus Gene Expression in Single Infected Insect Cells," *Biotechnology* 10:565–568 (1992).

Kinsey, et al., "Endoscopic System for Simultaneous Visual Examination and Electronic Detection of Fluorescence," *Rev. Sci. Instrum* 51(10):1403–1406 (1980).

Korpela, et al., "Stable Light Emitting *Escherichia coli* as a Biosensor," *Journal of Bioluminescence and Chemiluminescence* 4:551–554 (1989).

Kuhn, et al., "Intraoperative Gamma Detection Probe with Presurgical Antibody Imaging in Colon Cancer," *Arch Surg.* 126:1398–1403 (1991).

Langridge, et al., "Low–light Image Analysis of Transgenic Organism Using Bacterial Luciferase as a Marker," *Journal of Bioluminence Chemiluminence* 9(3):185–200 (1994).

Lanzafame et al., "Hemotoporphyrin Derivative Fluorescence: Photographic Techniques for the Localization of Malignant Tissue," *Lasers in Surgery and Medicine* 6:328:335 (1986).

Mach et al., "In vivo Localisation of Radiolabelled Antibodies to Carcinoembryonic Antigen in Human Colon Carcinoma Grafted into Nude Mice," *Nature* 248:704–706 (1974).

Mackey et al., "Thermostability of Bacterial Luciferase Expressed in Different Microbes," *J. Appl. Bacteriol.* 77:149–54 (1994).

Mang et al., "Fluorescence Detection of Tumors." *Cancer* 71:269–376 (1993).

McCormick et al., "Intracerebral Penetration of Infrared Light," *J. Neurosurg* 76:315–318 (1992).

Meighen, "Bacterial Bioluminescence: Organization, Regulation and Application of the lux Genes," *The FASEB Journal* 7:1016–1022 (1993).

Mew et al., "Photoimmunotherapy: Treatment of Animal Tumors with Tumor–Specific Monoclonal Antibody–Hematoporphyrin Conjugates," *Journal of Immunology* 130(3):1473–1477 (1983).

Montan et al., "Multicolor Imaging and Contrast Enhancement in Cancer–tumor Localization Using Laser–Induced Fluorenscence in Hematoporphyrin–Derivative–Bearing Tissue," *Optics Letters* 10(2):56–58 (1985).

Morrey et al., "Activation of the Human Immunodeficiency Virus Long Terminal Repeat by Abrasion of the Skin in Transgenic Mice" *Intervirology* 37(6):315–20 (1994).

Mueller–Kliesser and Walenta, "Geographical Mapping of Metabolites in Biological Tissue with Quantitative Bioluminescence and Single Photon Imaging," *Histochemical Journal* 25:407–420 (1993).

Neiderreither et al., "Minimal DNA Sequences That Control the Cell Lineage–Specific Expression of the Proα2(i) Collagen Promoter in Transgenic Mice," *Journal of Cell Biology* 119(5): 1361–1370 (1992).

O'Kane et al., "Visualization of Bioluminescence as a Marker of Gene Expression in Rhizobuum–Infected Soybean Root Noodles," *Plant Molecular Biology* 10:387–399 (1988).

Pèlegrin et al., "Antibody–Fluorescien Conjugates for Photoimmunodiagnosis of Human Colon Carcinoma in Nude Mice," *Cancer* 67:2529–2537 (1991).

Profio, A., "Review of Fluorescence Diagnosis Using Porphyrins," *SPIE* 907:150–156 (1988).

Profio, A.E., "Digital Background Subtraction for Fluorescence Imaging," *Med Phys* 13:717–721 (1986).

Schaefer et al., "Oxygentaion and Bioenergetic Status of Murine Fibrosarcomas," Oxygen Transport to Tissue XIV (Erdman, W. And D.f. Bruley), Eds., Plenum Press, New York, pp. 161–166 (1992).

Schneider et al., "The In Vivo Pattern of Firefly Luciferase Expression in Transgenic Plants," *Plant Molecular Biology* 14:935–947 (1990).

Shlyakhtina et al., "Radiations for the Mouse Liver at Normal Temperature and on Cooling," *Biophysics* 17(6):1146–1150 (1972).

Shtrankfel'd et al., "Very Weak Luminescence of Muscles," *Biophysics* 13(5): 1082–1084 (1968).

Steen et al., "In Vivo Measurement of Tumor Blood Oxygenation by Near Infrared Spectroscopy: Immediate Effects of Pentobarbital Overdose or Armustine Treatment," *J Neurooncol* 22:209–220 ( 1994).

Stewart et al., "lux Genes and the Applications of Bacterial Bioluminescence" *Journal of General Microbiology* 138:1289–1200 ( 1992).

Stone et al., "Oxygen in Human Tumors: Correlations Between Methods of Measurement and Response to Therapy," *Radiation Research* 136:422–434 (1993).

Straight et al., "Application of Charge Coupled Device Technology for Measurement of Laser Light and Fluorescence Distribution in Tumors for Photodynamic Therapy," *Photochemistry and Photobiology* 53(6):787–796 (1991).

Tamiya et al., "Spatial Imaging of Luciferase Gene Expression in Transgenic Fish," *Nucleic Acids Research* 18(4):1072 ( 1990).

Tang et al., "Pulsed and cw Laser Fluorescence Spectra from Cancerous, Normal, and Chemically Treated Normal Human Breast and Lung Tissues" *Applied Optics* 28(12): 2337–2342 (1989).

Tang et al., "Spectroscopic Difference Between Human Cancer and Normal Lung and Breast Tissues," *Lasers in Surgery and Medicine* 9:290–295 (1989).

Tatsu et al., "Homogeneous Chemiluminescent Immunoassay Based on Complement–Mediated Hemolysis of Red Blood Cells," *Analytical Chemistry* 62:2103–2106 (1990).

Van Mijk et al., "Regulatory Aspects of Low Intensity Photon Emission", *Experientia* 44:586–593 (1988).

Wagnierès et al., Photodetection of Early Cancer by Laser Fluorescence of a Tumor–selective Dye: Apparatus Design and Realization: *SPIE* 1203:43–52 (1990).

Wagnierès et al., "Photodetection of Early Cancer in the Upper Aerodigestive Tract and the Bronchi Using Photofrin Ii and Colorectal Adenocarcinoma with Fluoresceinated Monoclonal Antibodies," *SPIE* 1525:219–236 (1991).

Wilson et al., "Optical Reflectance and Transmittance of Tissues: Principles and Applications," *IEE Journal of Quantum Electronics* 26(12):2186–2199 ( 1990).

Wolleycher S., "Detection or Identification of Microbes by Introduction and Expression of an Exogeneous Gene Encoding an Enzyme for a Bioluminescent System," *Faming Zhuanli Shenqing Research Co.* Abstract No. XP–002137206 (1989).

Wood et al., "Complementary DNA Coding Click Beetle Luciferases Can Elicit Bioluminescence of Different Colors," *Science* 244:700–702 (1989).

Yoo et al., "Imaging Objects Hidden in Scattering Media Using a Fluorescence—Absorption Technique," *Optics Letters* 16(16):1252–1254 (1991).

Zhang et al., "Luciferase Activity as a Marker of Tumor Burden and as an Indicator of Tumor Response to Antineoplastic Therapy in vivo," *Clinc. Exp. Metastasis* 12:87–92 (1994).

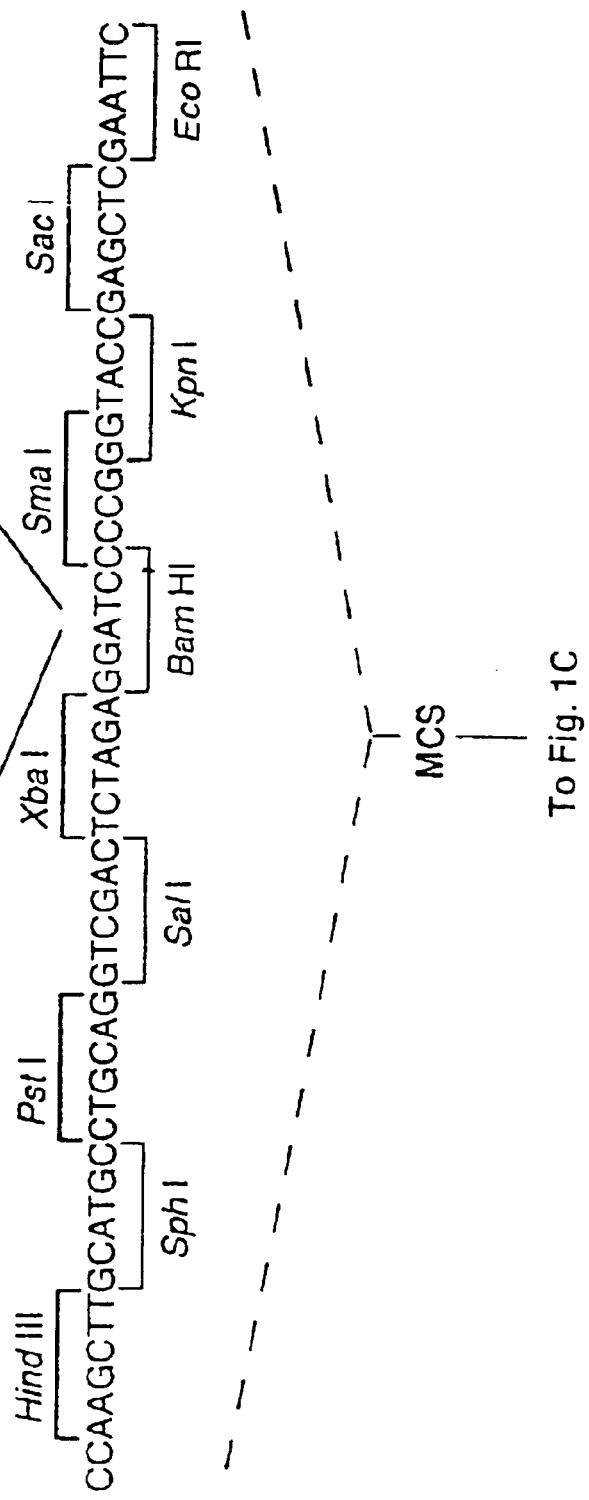

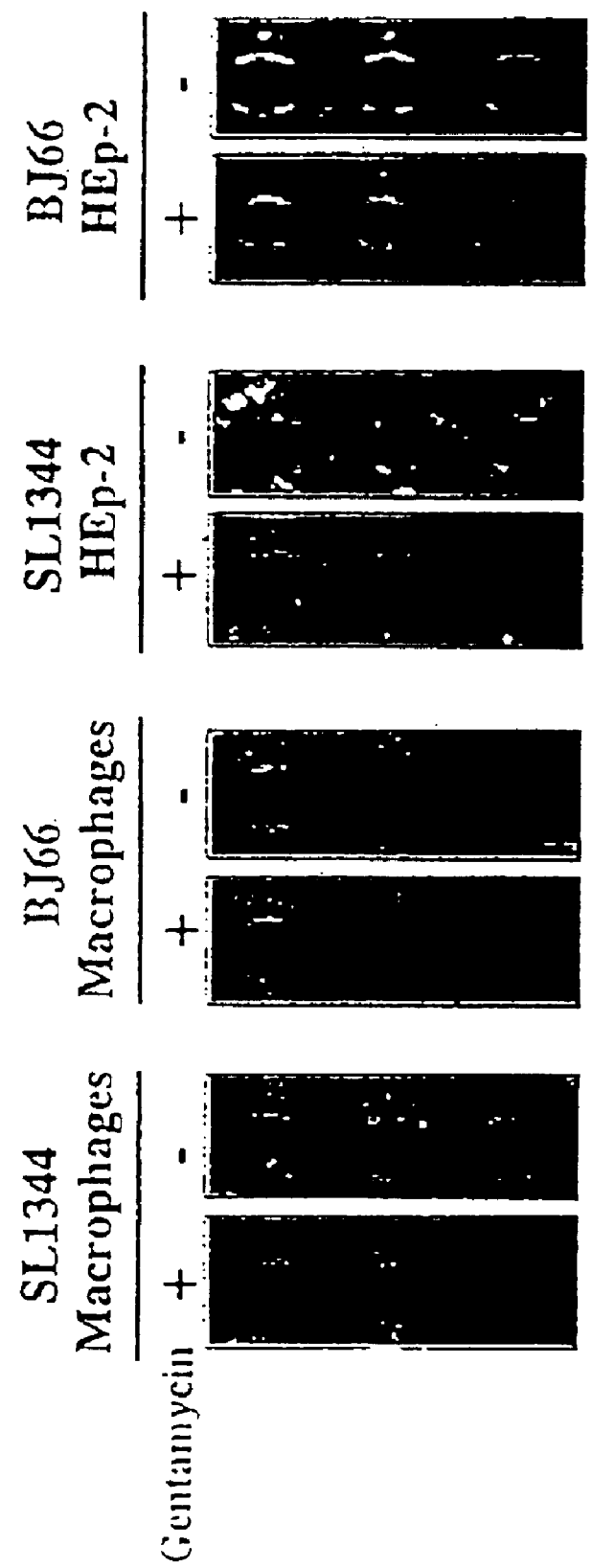

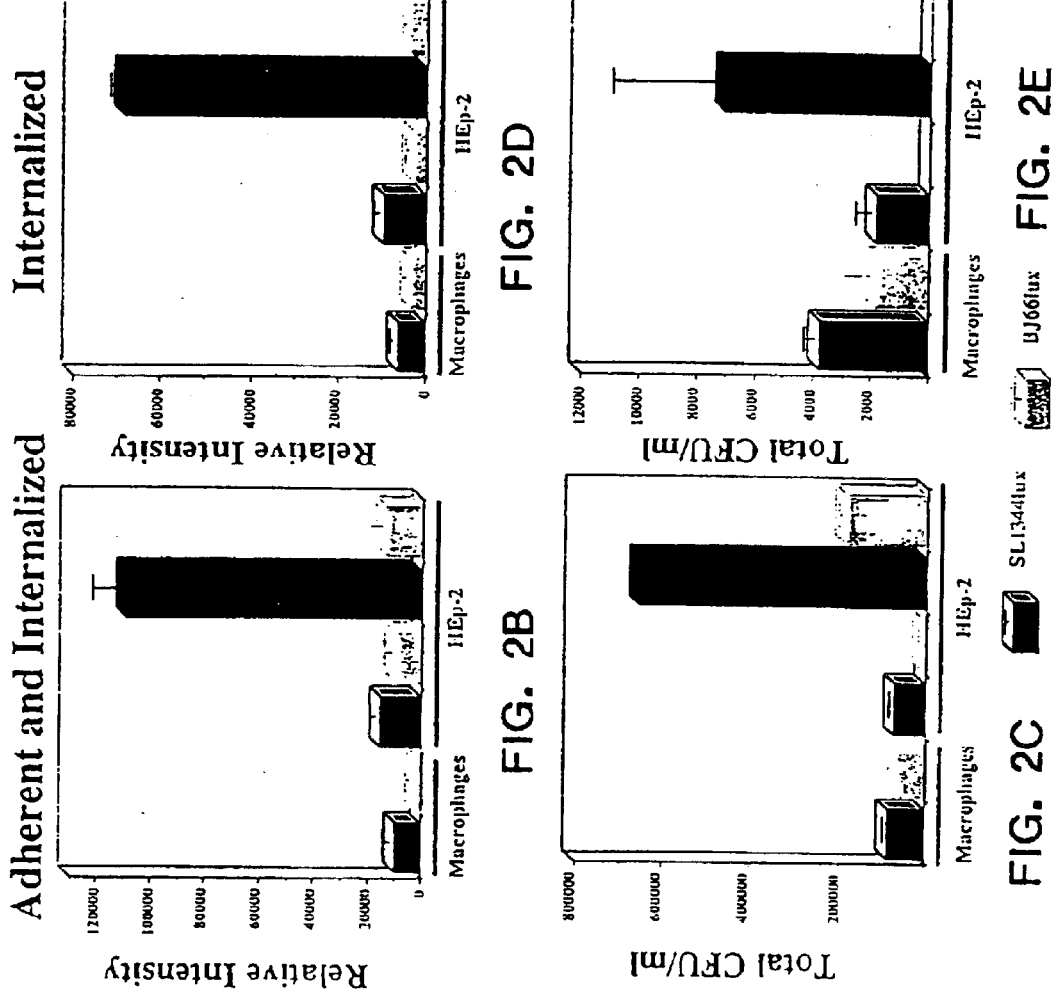

SL1344lux
(intraperitoneal)

Effect of Human Blood on Signal from Bioluminescent *Salmonella*

| Dilution | CFU/well | LB5000 Relative Bioluminescence | LB5000 and 30 µl blood Relative Bioluminescence |
|---|---|---|---|
| 1:100 | 512 | 199243 | 159497 |
| 1:200 | 256 | 187163 | 110081 |
| 1:400 | 128 | 170044 | 72234 |
| 1:800 | 64 | 154031 | 46273 |
| 1:1600 | 32 | 146934 | 17598 |
| 1:3200 | 16 | 112196 | 6731 |
| 1:6400 | 8 | 50302 | 320 |

FIG. 4

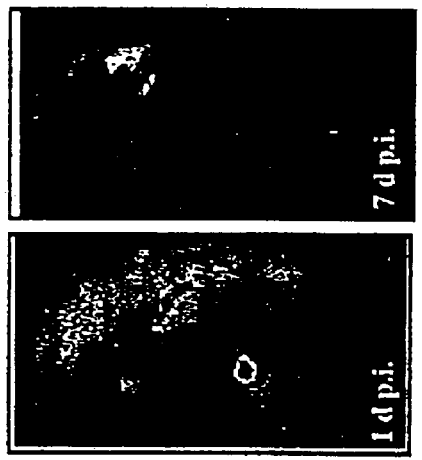
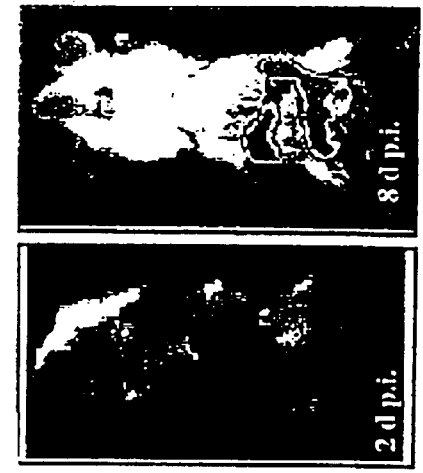
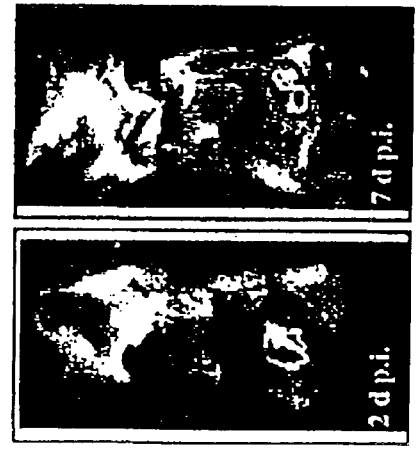
FIG. 6A  LB5000lux
FIG. 6B  BJ66lux
FIG. 6C  SL1344lux

FIG. 9C Air Injected
FIG. 9B Internal
FIG. 9A External
BJ66lux Infection (7 d p.i.)

Time post treatment: 0    5.5 h

Untreated

Treated

NON-INVASIVE LOCALIZATION OF A LIGHT-EMITTING CONJUGATE IN A MAMMAL

This application is a divisional application of U.S. Ser. No. 09/233,698, filed 19 Jan. 1999, now U.S. Pat. No. 6,649,143, which is a continuation of U.S. Ser. No. 08/602,396, filed 16 Feb. 1996, now abandoned, which is a continuation-in-part of U.S. Ser. No. 08/270,631, filed 1 Jul. 1994, now U.S. Pat. No. 5,650,135, from which priority is claimed under 35 U.S.C. § 120, and which applications are herein incorporated by reference in their entireties. This application is related to U.S. Ser. No. 09/233,507, filed 19 Jan. 1999, now U.S. Pat. No. 6,217,847, herein incorporated by reference in its entirety.

STATEMENT REGARDING FEDERALLY SPONSORED RESEARCH OR DEVELOPMENT

This work was supported in part by grants from the Office of Naval Research (N-00014-91-C-0170), the National Institutes of Health (PHS M01-RR-00070-30/1 and RR-00081) and the United States Public Health Service. Accordingly, the United States Government has certain rights in this invention.

I. FIELD OF THE INVENTION

The present invention relates to noninvasive methods and compositions for detecting, localizing and tracking light-emitting entities and biological events in a mammalian subject.

II. BACKGROUND OF THE INVENTION

The ability to monitor the progression of infectious diseases is limited by the current ex vivo methods of detecting and quantifying infectious agents in tissues. The replication of an infectious agent in a host often involves primary, secondary and tertiary sites of replication. The sites of replication and the course that an infectious agent follows through these sites is determined by the route of inoculation, factors encoded by the host as well as determinants of the infecting agent.

Experience may offer, in some cases, an estimate of probable sites of replication and the progress of an infection. It is more often the case, however, that the sites of infection, and the pace of the disease are either not known or can only roughly be estimated. Moreover, the progression of an infectious disease, even in inbred strains of mice, is often individualized, and serial, ex vivo analyses of many infected animals need to be conducted to determine, on the average, what course a disease will follow in an experimentally infected host.

Accordingly, it would be desirable to have a means of tracking the progression of infection in an animal model. Ideally, the tracking could be done non-invasively, such that a single animal could be evaluated as often as necessary without detrimental effects. Methods and compositions of the present invention provide a non-invasive approach to detect, localize and track a pathogen, as well as other entities, in a living host, such as a mammal.

III. SUMMARY OF THE INVENTION

In one embodiment, the invention includes a noninvasive method for detecting the localization of a biocompatible entity in a mammalian subject. The entity can be a molecule, macromolecule, cell, microorganism (including a pathogen), a particle, or the like.

The method includes administering to the subject a conjugate of the entity and a light-generating moiety. Light-generating moieties are typically molecules or macromolecules that give off light. They may generate light as a result of radiation absorption (e.g., fluorescent or phosphorescent molecules), or as a result of a chemical reaction (e.g., bioluminescent proteins). Exemplary light-generating moieties are bioluminescent proteins, such as luciferase and aequorin, and colored or fluorescent proteins, such as yellow fluorescent protein and ferredoxin IV.

The moiety may be conjugated to the entity by a variety of techniques, including incorporation during synthesis of the entity (e.g., chemical or genetic, such a fusion protein of an antibody fragment and a light-generating protein), chemical coupling post-synthesis, non-covalent association (e.g., encapsulation by liposomes), in-situ synthesis in the entity (e.g., expression of a heterologous bioluminescent protein in a transformed cell), or in situ activatable promoter-controlled expression of a bioluminescent protein in cells of a transgenic animal stimulated by a promoter inducer (e.g., interferon-activated promoter stimulated by infection with a virus).

After a period of time in which the conjugate can localize in the subject, the subject is immobilized within the detection field of a photodetector device for a period of time effective to measure a sufficient amount of photon emission (with the photodetector device) to construct an image. An exemplary photodetector device is an intensified charge-coupled device (ICCD) camera coupled to an image processor. If the image can be constructed in a time short relative to the time scale at which an "unimmobilized" subject moves, the subject is inherently "immobilized" during imaging and no special immobilization precautions are required. An image from the photon emission data is then constructed.

The method described above can be used to track the localization of the entity in the subject over time, by repeating the imaging steps at selected intervals and constructing images corresponding to each of those intervals.

The method described above can be used in a number of specific applications, by attaching, conjugating or incorporating targeting moieties onto the entity. The targeting moiety may be an inherent property of the entity (e.g., antibody or antibody fragment), or it may be conjugated to, attached to, or incorporated in the entity (e.g., liposomes containing antibodies). Examples of targeting moieties include antibodies, antibody fragments, enzyme inhibitors, receptor-binding molecules, various toxins and the like. Targets of the targeting moiety may include sites of inflammation, infection, thrombotic plaques and tumor cells. Markers distinguishing these targets, suitable for recognition by targeting moieties, are well known.

Further, the method may be used to detect and localize sites of infection by a pathogen in an animal model, using the pathogen (e.g., *Salmonella*) conjugated to a light-generating moiety as the entity.

In a related embodiment, the invention includes a noninvasive method for detecting the level of a biocompatible entity in a mammalian subject over time. The method is similar to methods described above, but is designed to detect changes in the level of the entity in the subject over time, without necessarily localizing the entity in the form of an image. This method is particularly useful for monitoring the effects of a therapeutic substance, such an antibiotic, on the levels of an entity, such as a light-emitting bacterium, over time.

In another embodiment, the invention includes a noninvasive method for detecting the integration of a transgene in a mammalian subject. The method includes administering to the subject, a vector construct effective to integrate a transgene into mammalian cells. Such constructs are well known in the art. In addition to the elements necessary to integrate effectively, the construct contains a transgene (e.g., a therapeutic gene), and a gene encoding a light-generating protein under the control of a selected activatable promoter. After a period of time in which the construct can achieve integration, the promoter is activated. For example, if an interferon inducible promoter is used, a poly-inosine and -cytosine duplex (poly-IC) can be locally administered (e.g., footpad injection) to stimulate interferon production. The HIV LTR could similarly be used and induced, for example, with dimethylsulfoxide (DMSO). The subject is then placed within the detection field of a photodetector device, such as an individual wearing light-intensifying "night vision" goggles, and the level of photon emission is measured, or evaluated. If the level is above background (i.e., if light can be preferentially detected in the "activated" region), the subject is scored as having integrated the transgene.

In a related embodiment, the invention includes a noninvasive method for detecting the localization of a promoter-induction event in an animal made transgenic or chimeric for a construct including a gene encoding a light-generating protein under the control of an inducible promoter. Promoter induction events include the administration of a substance which directly activates the promoter, the administration of a substance which stimulates production of an endogenous promoter activator (e.g., stimulation of interferon production by RNA virus infection), the imposition of conditions resulting in the production of an endogenous promoter activator (e.g., heat shock or stress), and the like. The event is triggered, and the animal is imaged as described above.

In yet another embodiment, the invention includes pathogens, such as *Salmonella*, transformed with a gene expressing a light-generating protein, such as luciferase.

In another aspect, the invention includes a method of identifying therapeutic compounds effective to inhibit spread of infection by a pathogen. The method includes administering a conjugate of the pathogen and a light-generating moiety to control and experimental animals, treating the experimental animals with a putative therapeutic compound, localizing the light-emitting pathogen in both control and experimental animals by the methods described above, and identifying the compound as therapeutic if the compound is effective to significantly inhibit the spread or replication of the pathogen in the experimental animals relative to control animals. The conjugates include a fluorescently-labeled antibodies, fluorescently-labeled particles, fluorescently-labeled small molecules, and the like.

In still another aspect, the invention includes a method of localizing entities conjugated to light-generating moieties through media of varying opacity. The method includes the use of photodetector device to detect photons transmitted through the medium, integrate the photons over time, and generate an image based on the integrated signal.

In yet another embodiment, the invention includes a method of measuring the concentration of selected substances, such as dissolved oxygen or calcium, at specific sites in an organism. The method includes entities, such as cells, containing a concentration sensor—a light-generating molecule whose ability to generate light is dependent on the concentration of the selected substance. The entity containing the light-generating molecule is administered such that it adopts a substantially uniform distribution in the animal or in a specific tissue or organ system (e.g., spleen). The organism is imaged, and the intensity and localization of light emission is correlated to the concentration and location of the selected substance. Alternatively, the entity contains a second marker, such as a molecule capable of generating light at a wavelength other than the concentration sensor. The second marker is used to normalize for any non-uniformities in the distribution of the entity in the host, and thus permit a more accurate determination of the concentration of the selected substance.

In another aspect, the invention includes a method of identifying therapeutic compounds effective to inhibit the growth and/or the metastatic spread of a tumor. The method includes (i) administering tumor cells labeled with or containing light-generating moieties to groups of experimental and control animals, (ii) treating the experimental group with a selected compound, (iii) localizing the tumor cells in animals from both groups by imaging photon emission from the light-generating molecules associated with the tumor cells with a photodetector device, and (iv) identifying a compound as therapeutic if the compound is able to significantly inhibit the growth and/or metastatic spread of the tumor in the experimental group relative to the control group.

These and other objects and features of the invention will be more fully appreciated when the following detailed description of the invention is read in conjunction with the accompanying drawings.

IV. BRIEF DESCRIPTION OF THE DRAWINGS

FIGS. 1A, 1B and 1C show a map of the lux pCGLS1 plasmid used to transform *Salmonella* strains SL1344, BJ66 and LB5000 to generate strains SL1344lux, BJ66lux and LB5000lux. FIG. 1A depicts a restriction enzyme map of the lux operon, which is inserted into the BamHI site of the polylinker depicted in FIG. 1B. A sequence included in the multiple cloning site (MCS) is provided in FIG. 1B, with the Bam HI site indicated in bold type. A graphical representation of a pUC18 vector without insert is shown in FIG. 1C.

FIGS. 2A, 2B, 2C, 2D and 2E depict the adherence and invasion of *Salmonella* strains SL1344lux and BJ66lux on macrophages and HEp-2 cells.

FIG. 2A depicts luminescent bacterial cells localized in wells of an assay dish. The pseudo-color image, obtained by integrating photons over one minute, is superimposed over a gray scale image of the assay dish, producing the "composite image" shown.

FIG. 2B depicts the relative light intensity of wells that were not treated with gentamicin.

FIG. 2C depicts the number of colony forming units (CFU) per ml isolated from the same wells as were imaged in FIG. 2B.

FIG. 2D depicts the relative light intensity of wells that were treated with gentamicin.

FIG. 2E depicts the number of colony forming units (CFU) per ml isolated from the same wells as were imaged in FIG. 2D.

Figure 3A:
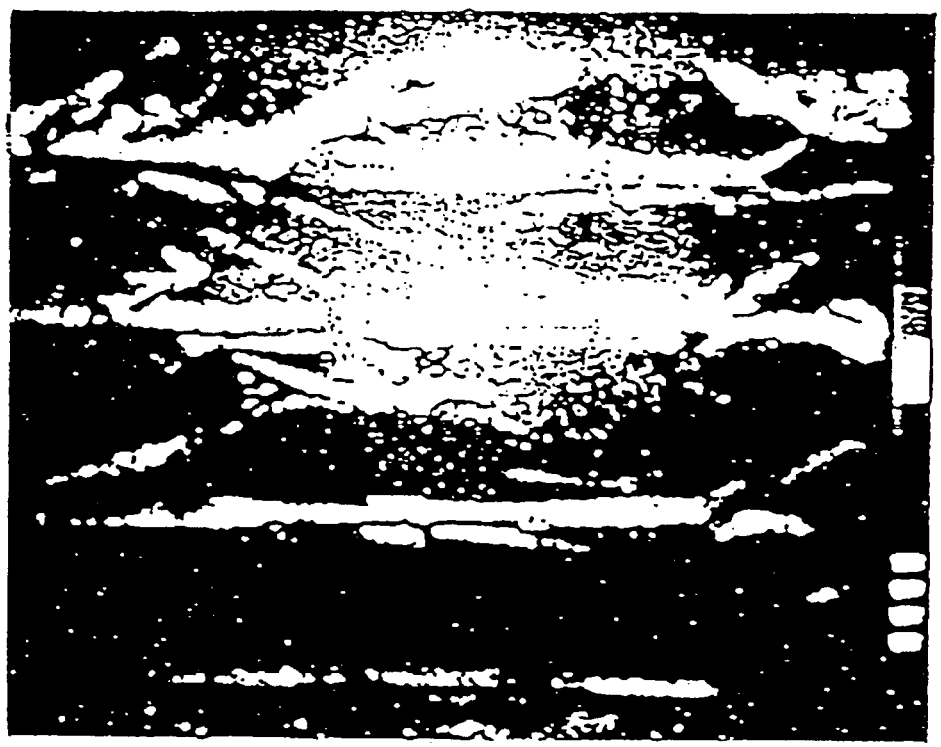

FIG. 3A depicts a composite image of four glass capillary tubes containing dilutions of LB5000lux bacterial suspensions. Luminescence was determined by integrating over 30 seconds. Air pockets are present in each tube on both sides of the suspension.

Figure 3B:

FIG. 3B depicts the distribution of bioluminescence following intraperitoneal inoculation of wild-type SL1344lux into mice.

FIG. 4 depicts the effect of human blood on the light emission from bioluminescent *Salmonella*.

Figure 5:
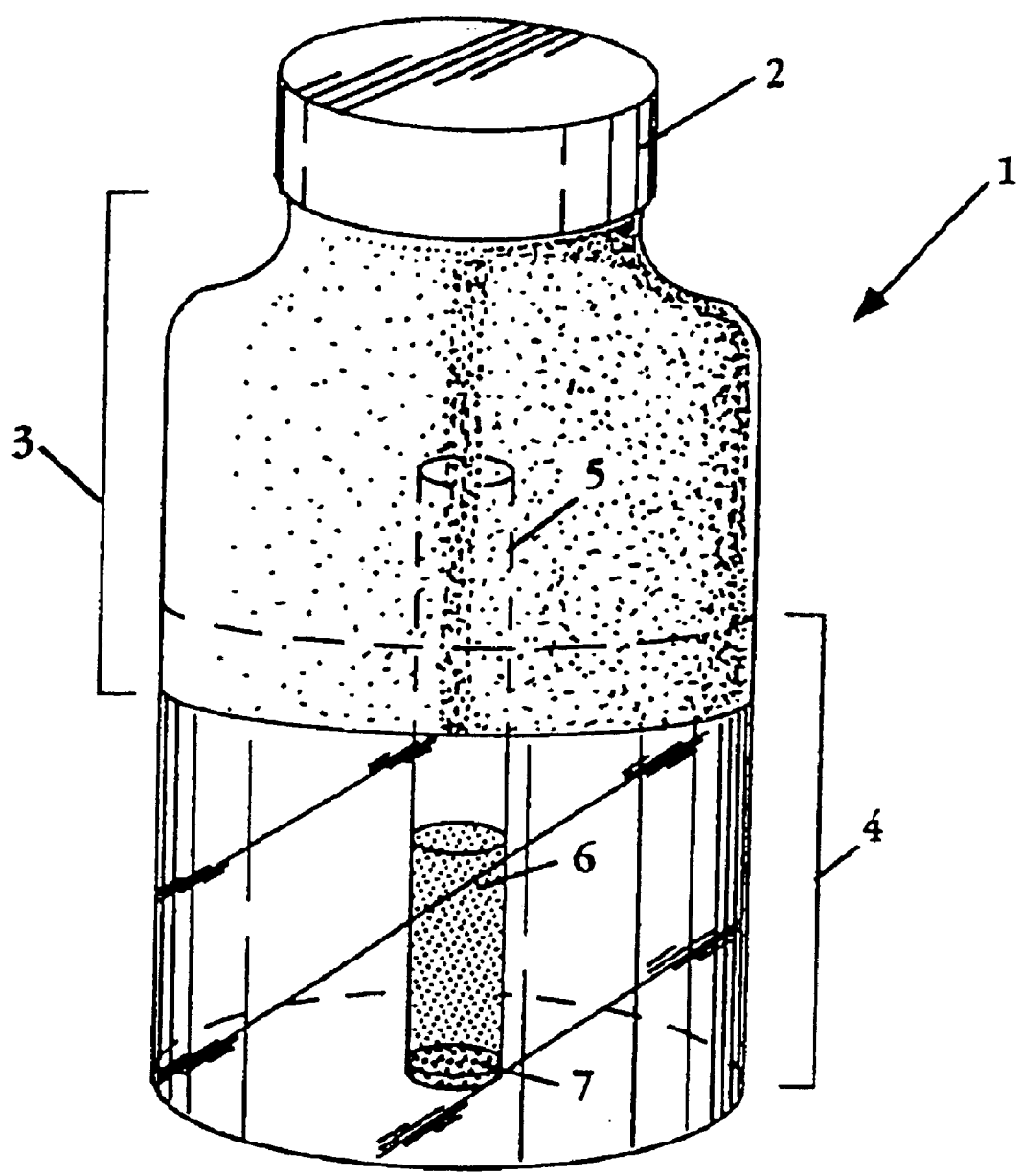

FIG. 5 depicts a schematic diagram of a vial used to test the transmission of light generated by LB5000lux through animal tissue.

FIG. 6A depicts composite images of Balb/c mice orally inoculated with low virulence LB5000lux *Salmonella*, and imaged at the times indicated. The luminescence signal was integrated over 5 minutes.

FIG. 6B depicts composite images of Balb/c mice orally inoculated withnon-invasive BJ66lux *Salmonella*, and imaged at the times indicated. The luminescence signal was integrated over 5 minutes.

FIG. 6C depicts composite images of Balb/c mice orally inoculated with virulent SL1344lux *Salmonella*, and imaged at the times indicated. The luminescence signal was integrated over 5 minutes.

Figure 7:

FIG. 7 depicts a composite image showing the distribution of *Salmonella* in mice 32 hours following intraperitoneal (i.p.) injections with either virulent SL1344lux (left two animals) or low virulence LB5000lux (right two animals) strains of the bacterium.

Figure 8A:

FIG. 8A depicts the distribution of virulent *Salmonella* in mice resistant to systemic *Salmonella* infections (129×Balb/c, Ity$^{r/s}$) on day one (1).

Figure 8B:

FIG. 8B depicts the distribution of virulent *Salmonella* in mice resistant to systemic *Salmonella* infections (129×Balb/c, Ity$^{r/s}$) on day eight (8).

FIGS. 9A, 9B, and 9C depict the distribution of mutant *Salmonella* with reduced virulence (BJ66lux) seven days following oral inoculation.

FIG. 9A depicts external, non-invasive imaging of the luminescence.

FIG. 9B depicts the same animal imaged following laparotomy. Labeled organs are cecum (C), liver (L), small intestine (I), and spleen (Sp).

FIG. 9C depicts a post-laparotomy image generated following injection of air into the lumen of the intestine both anterior and posterior to the cecum.

Figure 10C:
Figure 10B:
Figure 10A:
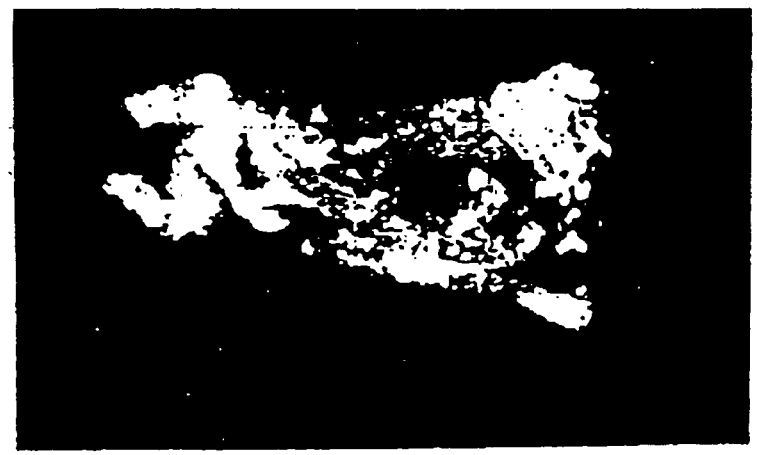

FIGS. 10A, 10B and 10C depict the distribution of *Salmonella* SL1344lux in susceptible Balb/c mice following intraperitoneal inoculation with SL1344lux.

FIG. 10A depicts an image prior to the opening of the peritaneal cavity.

FIG. 10B depicts an image after the opening of the peritoneal cavity.

FIG. 10C depicts an image after the cecum was pulled to the left side.

FIGS. 11A, 11B, 11C, 11D, and 11E depict the effects of ciprofloxacin treatment on bioluminescence from SL1344lux *Salmonella* in orally-inoculated mice.

Figure 11A:
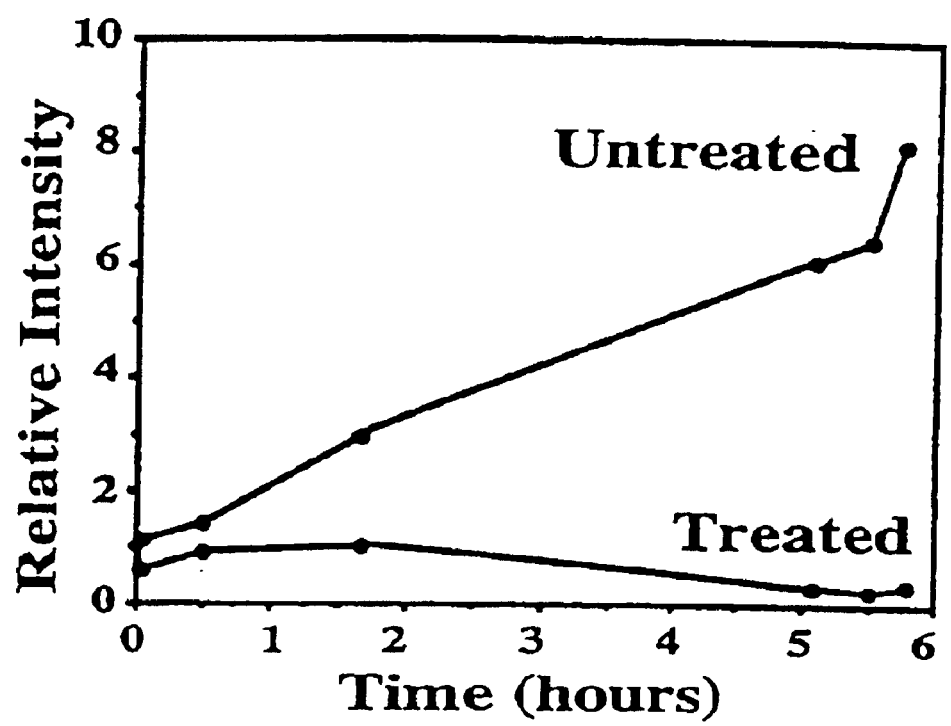

FIG. 11A shows a graph of the relative bioluminescence intensity, measured from the abdominal area, as a function of time after initiation of treatment, for treated and untreated animals.

Figures 11B, 11C:
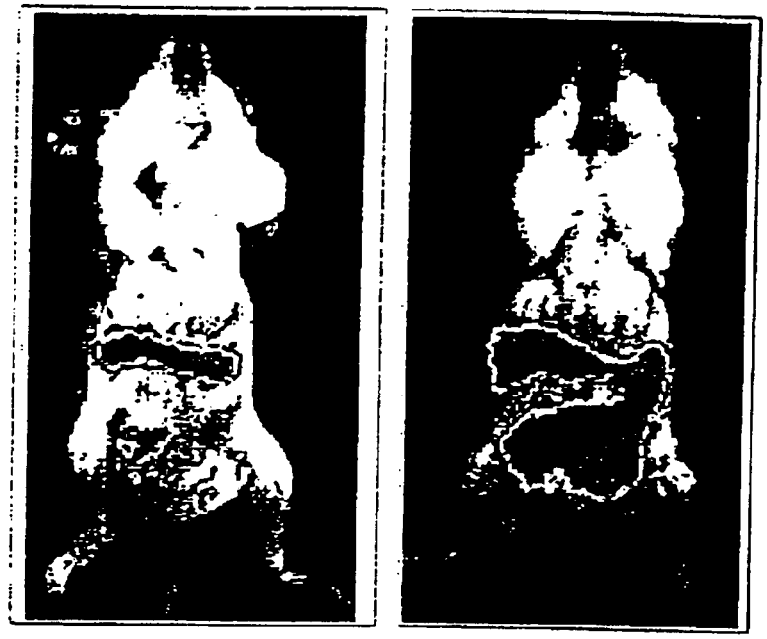
Figures 11D, 11E:
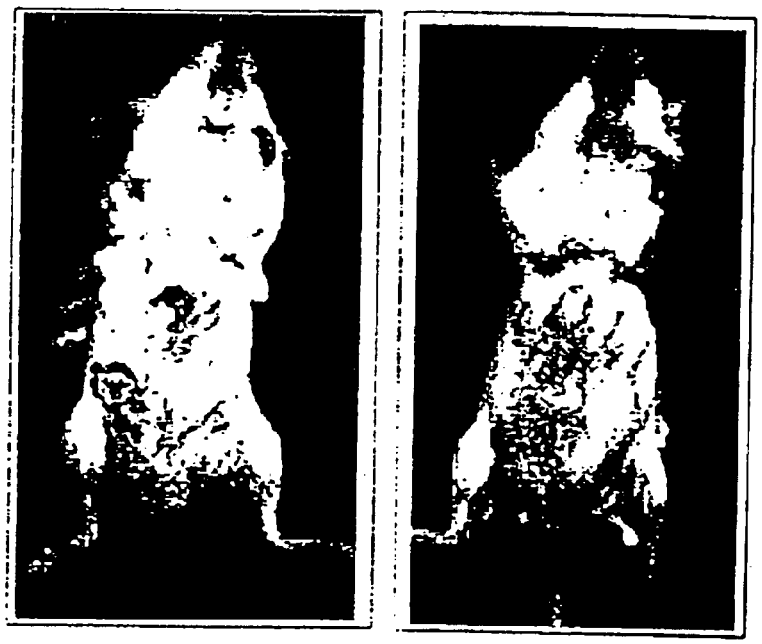

FIGS. 11B and 11D depict composite images of mice 8 days after oral inoculation with SL1344lux *Salmonella*, before treatment with ciprofloxacin.

FIGS. 11C and 11E depict composite images of the same mice 5.5 hours either following treatment (FIG. 11E) or control (no treatment: FIG. 11C).

Figure 12:
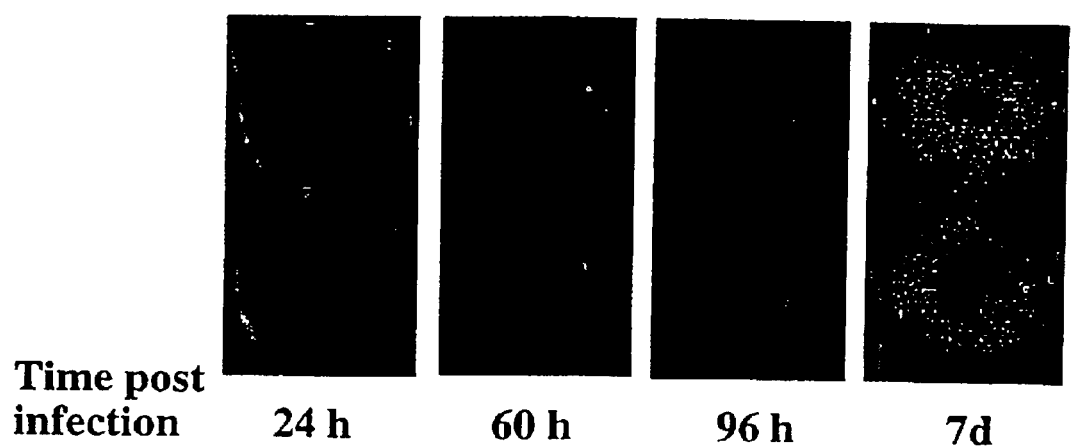

FIG. 12 depicts bioluminescence as a reporter for replication of HIV-1 in culture. The gray scale image of the plates at 24h, 60h, 96h, and 7d, as indicated, is shown.

Figure 13:
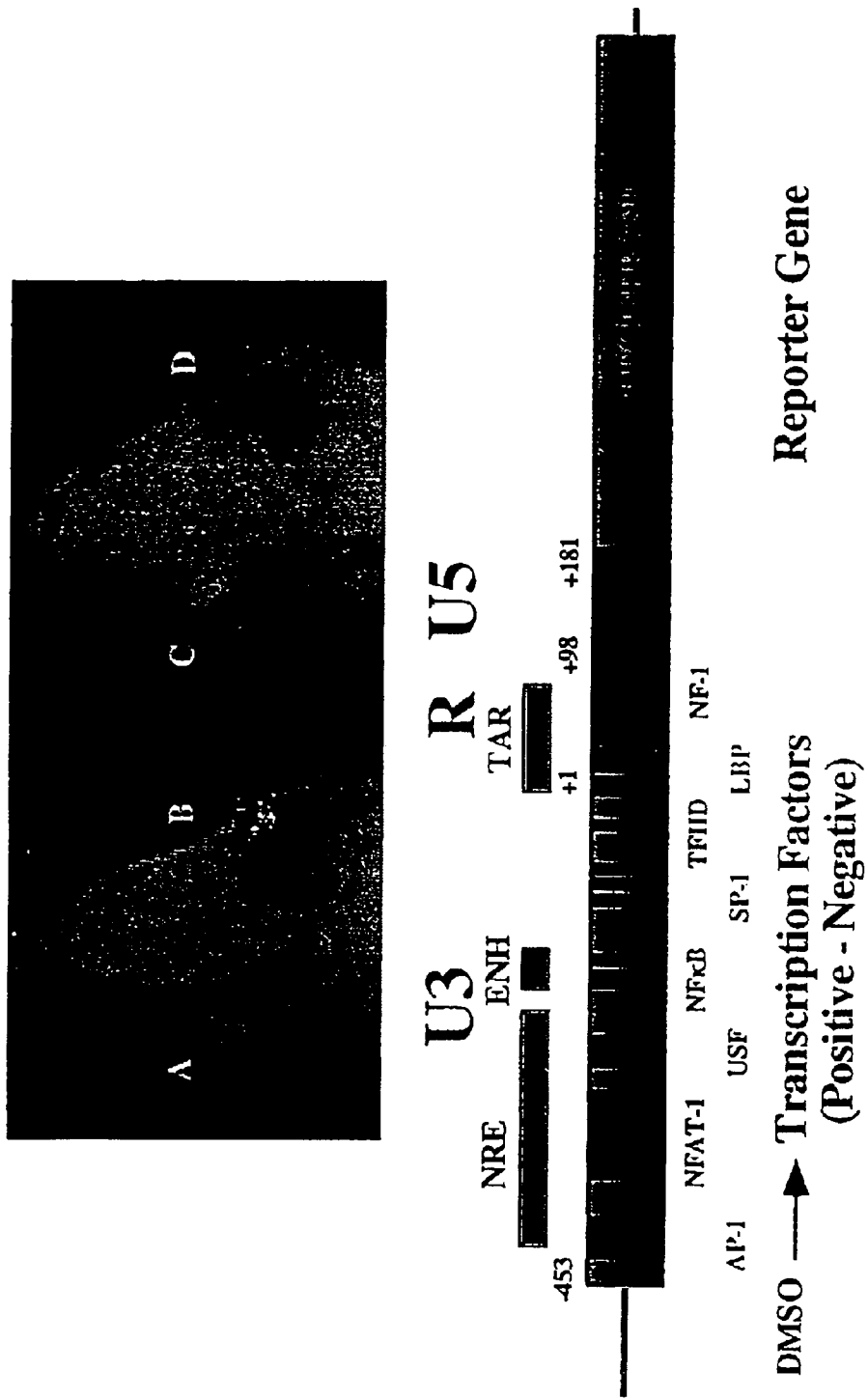

FIG. 13 depicts an assessment of the promoter activity in tissues of transgenic mice containing a construct composed of the regulatory portion of the HIV LTR (U3 region) upstream of the coding sequence of the firefly luciferase gene. NRE, negative response element; ENH, enhancer region, TAR-transactivation responsive element.

Figure 14:
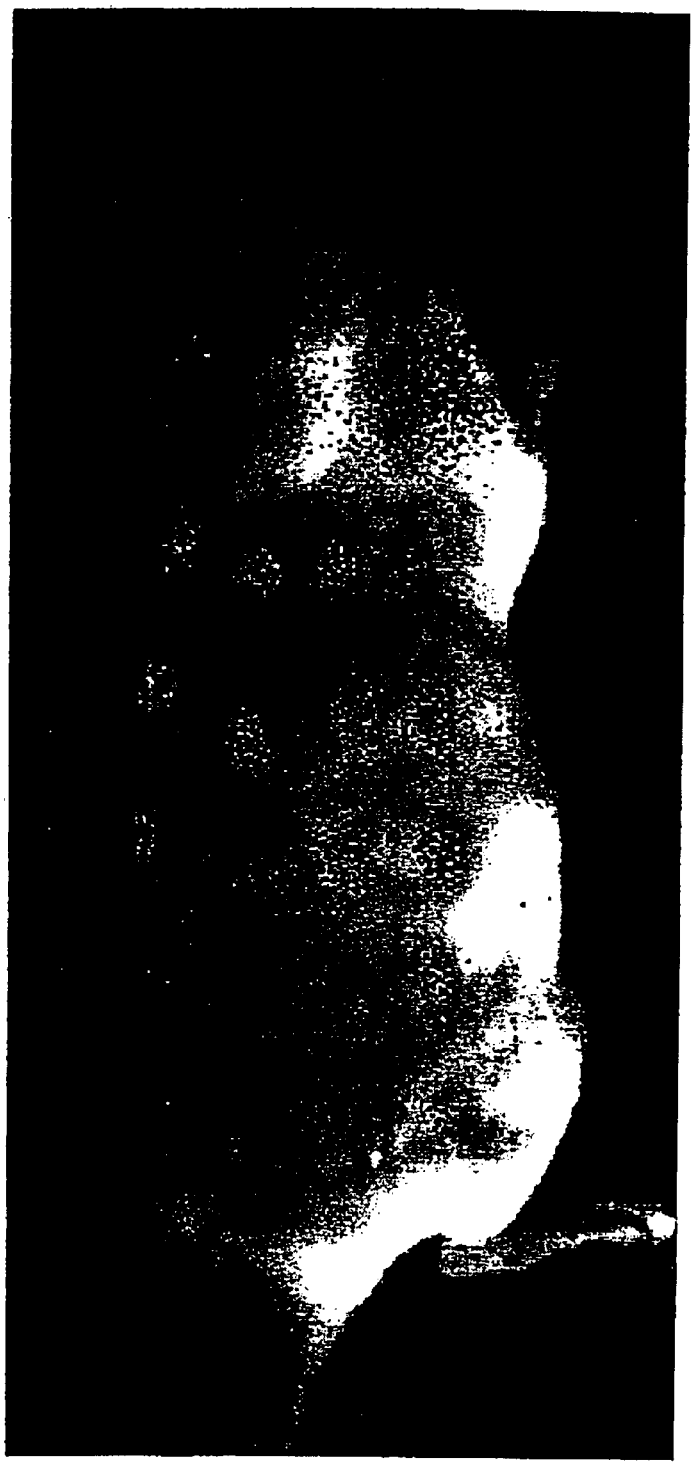

FIG. 14 depicts topical delivery of substrate to dermal cells in transgenic mice containing a construct composed of the regulatory portion of the HIV LTR upstream of the coding sequence of the firefly luciferase gene.

Figure 15:
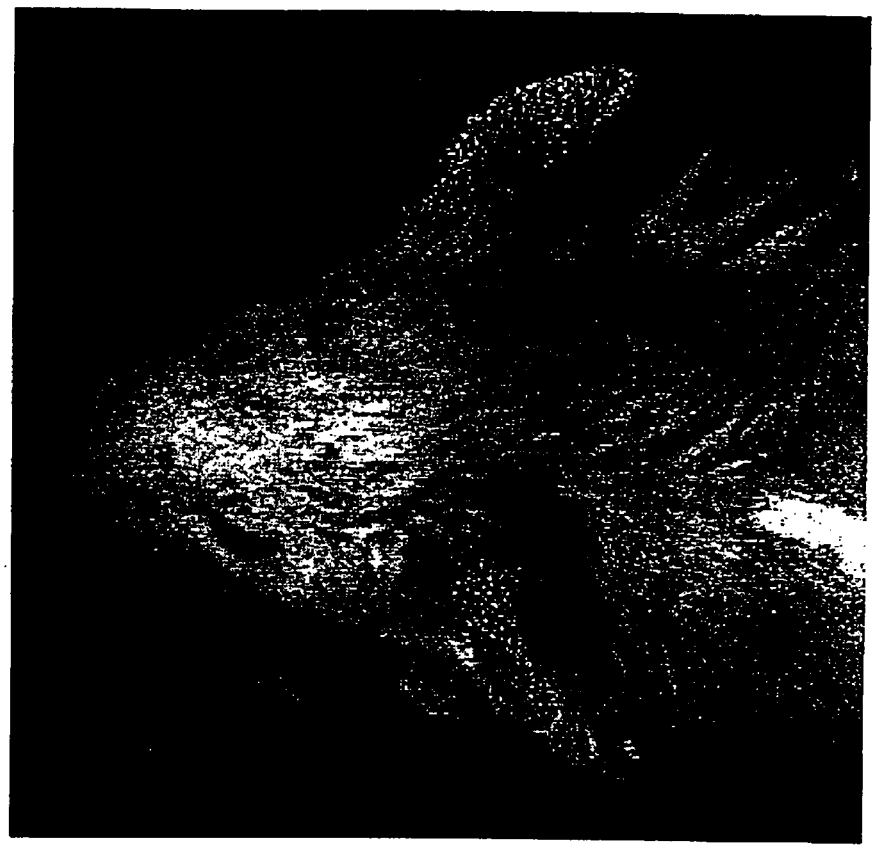

FIG. 15 depicts bioluminescence from induced ears as result of topical luciferin delivery in transgenic mice containing a construct composed of the regulatory portion of the HIV LTR upstream of the coding sequence of the firefly luciferase gene.

Figure 16:

FIG. 16 depicts unilateral induction of luciferase expression in transgenic mice; the left half of the shaved dorsal surface of the mice and the left ear were treated with DMSO to activate expression of the HIV-1 LTR; luciferin was applied topically over the entire surface of the back and both ears.

Figure 17:

FIG. 17 depicts the detection of bioluminescence from internal tissues in transgenic mice.

Figure 18:
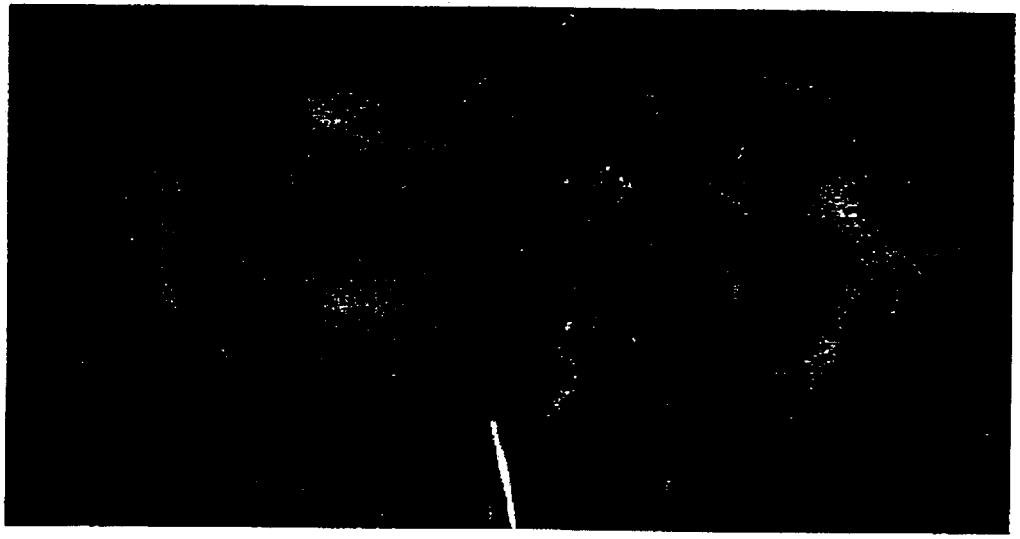

FIG. 18 depicts imaging of the abdomen of animals following laprotomy demonstrating signals to localize the origin of internal bioluminescence.

Figure 19:
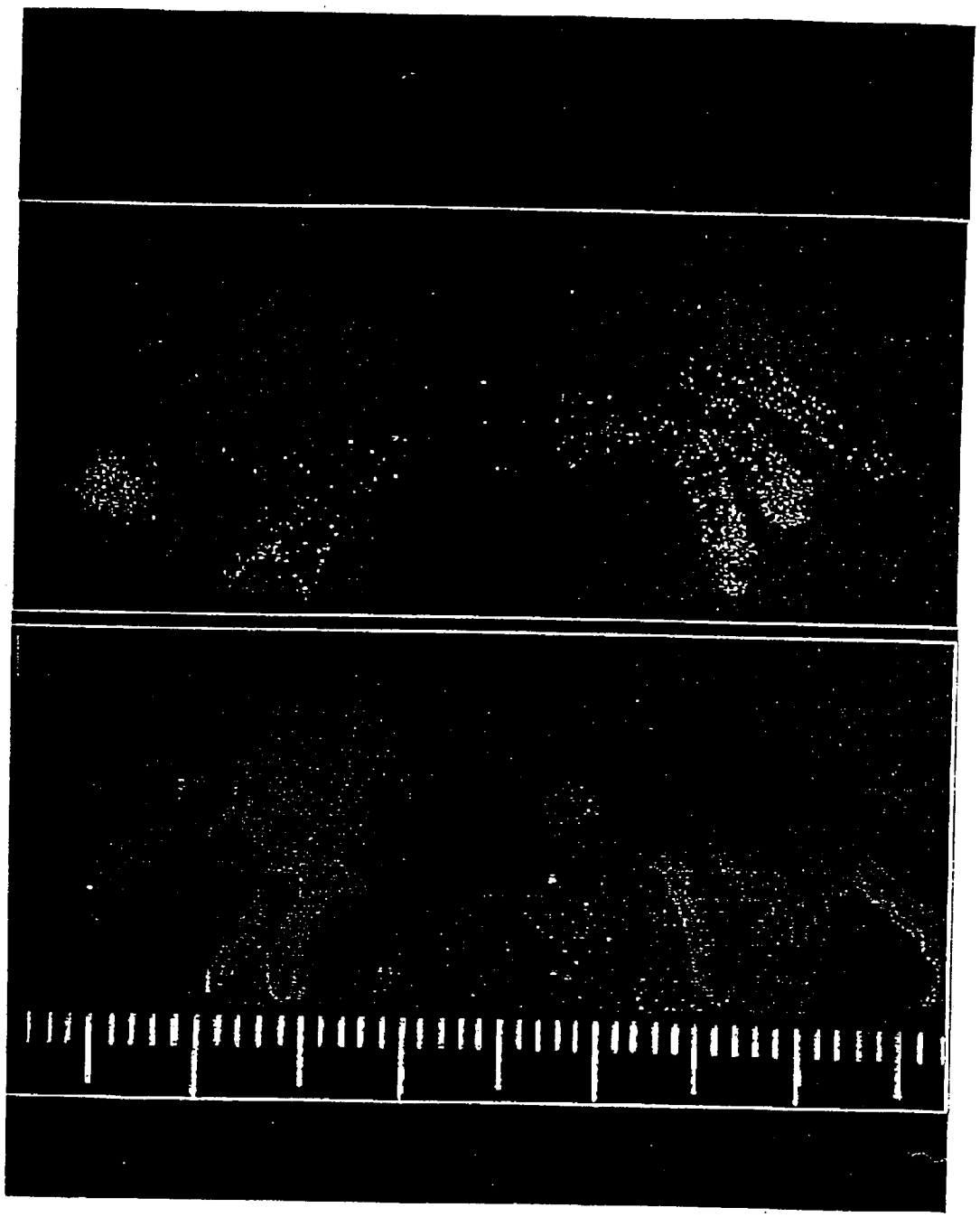

FIG. 19 depicts expression of the differential expression of HIV-LTR in neonatal transgenic mice.

V. DETAILED DESCRIPTION OF THE INVENTION

A. Definitions

Unless otherwise indicated, all terms used herein have the same meaning as they would to one skilled in the art of the present invention.

Opaque medium is used herein to refer to a medium that is "traditionally" opaque, not necessarily absolutely opaque. Accordingly, an opaque medium is defined as a medium that is commonly considered to be neither transparent nor translucent, and includes items such as a wood board, and flesh and skin of a mammal.

Luciferase, unless stated otherwise, includes prokaryotic and eukaryotic luciferases, as well as variants possessing varied or altered optical properties, such as luciferases that luminesce at wavelengths in the red range.

Biocompatible entity is an entity that can be administered to a mammal. This includes pathogens which may be deleterious to the mammal. In reference to an animal whose cells contain a transgene expressing a light-generating protein, biocompatible entity refers to the transgene-containing cells comprising the mammal.

Light-generating is defined as capable of generating light through a chemical reaction or through the absorption of radiation.

Light is defined herein, unless stated otherwise, as electromagnetic radiation having a wavelength of between about 300 nm and about 1100 nm.

Spread of infection typically refers to the spreading and colonization by a pathogen of host sites other than the initial infection site. The term can also include, however, growth in size and/or number of the pathogen at the initial infection site.

lux—prokaryotic genes associated with luciferase and photon emission.

luc—eukaryotic genes associated with luciferase and photon emission.

Promoter induction event refers to an event that results in the direct or indirect induction of a selected inducible promoter.

Heterologous gene refers to a gene which has been transfected into a host organism. Typically, a heterologous gene refers to a gene that is not originally derived from the transfected or transformed cells' genomic DNA.

Transgene refers to a heterologous gene which has been introduced, transiently or permanently, into the germ line or somatic cells of an organism.

B. General Overview of the Invention

The present invention includes methods and compositions relating to non-invasive imaging and/or detecting of light-emitting conjugates in mammalian subjects. The conjugates contain a biocompatible entity and a light-generating moiety. Biocompatible entities include, but are not limited to, small molecules such as cyclic organic molecules; macromolecules such as proteins; microorganisms such as viruses, bacteria, yeast and fungi; eukaryotic cells; all types of pathogens and pathogenic substances; and particles such as beads and liposomes. In another aspect, biocompatible entities may be all or some of the cells that constitute the mammalian subject being imaged.

Light-emitting capability is conferred on the entities by the conjugation of a light-generating moiety. Such moieties include fluorescent molecules, fluorescent proteins, enzymatic reactions giving off photons and luminescent substances, such as bioluminescent proteins. The conjugation may involve a chemical coupling step, genetic engineering of a fusion protein, or the transformation of a cell, microorganism or animal to express a bioluminescent protein. For example, in the case where the entities are the cells constituting the mammalian subject being imaged, the light-generating moiety may be a bioluminescent or fluorescent protein "conjugated" to the cells through localized, promoter-controlled expression from a vector construct introduced into the cells by having made a transgenic or chimeric animal.

Light-emitting conjugates are typically administered to a subject by any of a variety of methods, allowed to localize within the subject, and imaged. Since the imaging, or measuring photon emission from the subject, may last up to tens of minutes, the subject is usually, but not always, immobilized during the imaging process.

Imaging of the light-emitting entities involves the use of a photodetector capable of detecting extremely low levels of light—typically single photon events—and integrating photon emission until an image can be constructed. Examples of such sensitive photodetectors include devices that intensify the single photon events before the events are detected by a camera, and cameras (cooled, for example, with liquid nitrogen) that are capable of detecting single photons over the background noise inherent in a detection system.

Once a photon emission image is generated, it is typically superimposed on a "normal" reflected light image of the subject to provide a frame of reference for the source of the emitted photons (i.e., localize the light-emitting conjugates with respect to the subject). Such a "composite" image is then analyzed to determine the location and/or amount of a target in the subject.

The steps and embodiments outlined above are presented in greater detail, below.

C. Light-Emitting Entities

1. Light-Generating Moieties.

The light-generating moieties (LGMs), molecules or constructs useful in the practice of the present invention may take any of a variety of forms, depending on the application. They share the characteristic that they are luminescent, that is, that they emit electromagnetic radiation in ultraviolet (UV), visible and/or infra-red (IR) from atoms or molecules as a result of the transition of an electronically excited state to a lower energy state, usually the ground state.

Examples of light-generating moieties include photoluminescent molecules, such as fluorescent molecules, chemiluminescent compounds, phosphorescent compounds, and bioluminescent compounds.

Two characteristics of LGMs that bear considerable relevance to the present invention are their size and their spectral properties. Both are discussed in the context of specific types of light-generating moieties described below, following a general discussion of spectral properties.

Spectral Properties. An important aspect of the present invention is the selection of light-generating moieties that produce light capable of penetrating animal tissue such that it can be detected externally in a non-invasive manner. The ability of light to pass through a medium such as animal tissue (composed mostly of water) is determined primarily by the light's intensity and wavelength.

The more intense the light produced in a unit volume, the easier the light will be to detect. The intensity of light produced in a unit volume depends on the spectral characteristics of individual LGMs, discussed below, and on the concentration of those moieties in the unit volume. Accordingly, conjugation schemes that place a high concentration of LGMs in or on an entity (such as high-efficiency loading of a liposome or high-level expression of a bioluminescent protein in a cell) typically produce brighter light-emitting conjugates (LECs), which are easier to detect through deeper layers of tissue, than schemes which conjugate, for example, only a single LGM onto each entity.

A second factor governing the detectability of an LGM through a layer of tissue is the wavelength of the emitted light. Water may be used to approximate the absorption characteristics of animal tissue, since most tissues are composed primarily of water. It is well known that water transmits longer-wavelength light (in the red range) more readily than it does shorter wavelength light.

Accordingly, LGMs which emit light in the range of yellow to red (550–1100 nm) are typically preferable to LGMs which emit at shorter wavelengths. Several of the LGMs discussed below emit in this range. However, it will be noted, based on experiments performed in support of the present invention and presented below, that excellent results can be achieved in practicing the present invention with LGMs that emit in the range of 486 nm, despite the fact that this is not an optimal emission wavelength. These results are possible, in part, due to the relatively high concentration of LGMs (luciferase molecules) present in the LECs (transformed *Salmonella* cells) used in these experiments, and to the use of a sensitive detector. It will be understood that through the use of LGMs with a more optimal emission wavelength, similar detection results can be obtained with LGEs having lower concentrations of the LGMs.

Fluorescence-based Moieties. Fluorescence is the luminescence of a substance from a single electronically excited state, which is of very short duration after removal of the source of radiation. The wavelength of the emitted fluorescence light is longer than that of the exciting illumination (Stokes' Law), because part of the exciting light is converted into heat by the fluorescent molecule.

Because fluorescent molecules require input of light in order to luminesce, their use in the present invention may be more complicated than the use of bioluminescent molecules. Precautions are typically taken to shield the excitatory light so as not to contaminate the fluorescence photon signal being detected from the subject. Obvious precautions include the placement of an excitation filter, such that employed in fluorescence microscope, at the radiation source. An appropriately-selected excitation filter blocks the majority of photons having a wavelength similar to that of the photons emitted by the fluorescent moiety. Similarly a barrier filter is employed at the detector to screen out most of the photons having wavelengths other than that of the fluorescence photons. Filters such as those described above can be obtained from a variety of commercial sources, including Omega Optical, Inc. (Brattleboro, Vt.).

Alternatively, a laser producing high intensity light near the appropriate excitation wavelength, but not near the fluorescence emission wavelength, can be used to excite the fluorescent moieties. An x-y translation mechanism may be employed so that the laser can scan the subject, for example, as in a confocal microscope.

As an additional precaution, the radiation source can be placed behind the subject and shielded, such that the only radiation photons reaching the site of the detector are those that pass all the way through the subject. Furthermore, detectors may be selected that have a reduced sensitivity to wavelengths of light used to excite the fluorescent moiety.

Through judicious application of the precautions above, the detection of fluorescent LGMs according to methods of the present invention is possible.

Fluorescent moieties include small fluorescent molecules, such as fluorescein, as well as fluorescent proteins, such as green fluorescent protein (Chalfie, et al., 1994, *Science* 263:802–805., Morin and Hastings, 1971, *J. Cell. Physiol.* 77:313) and lumazine and yellow fluorescent proteins (O'Kane, et al., 1991, *PNAS* 88:1100–1104, Daubner, et al., 1987, *PNAS* 84:8912–8916). In addition, certain colored proteins such as ferredoxin IV (Grabau, et al., 1991, *J Biol Chem.* 266:3294–3299), whose fluorescence characteristics have not been evaluated, may be fluorescent and thus applicable for use with the present invention. Ferredoxin IV is a particularly promising candidate, as it has a reddish color, indicating that it may fluoresce or reflect at a relatively long wavelength and produce light that is effective at penetrating tissue. Furthermore, the molecule is small for a protein (95 amino acids), and can thus be conjugated to entities with a minimal impact on their function.

An advantage of small fluorescent molecules is that they are less likely to interfere with the bioactivity of the entity to which they are attached than a would a larger light-generating moiety. In addition, commercially-available fluorescent molecules can be obtained with a variety of excitation and emission spectra that are suitable for use with the present invention. For example, Molecular Probes (Eugene, Oreg.) sells a number of fluorophores, including Lucifer Yellow (abs. at 428 nm, and emits at 535 nm) and Nile Red (abs. at 551 nm and emits at 636 nm). Further, the molecules can be obtained derivatized with a variety of groups for use with various conjugation schemes (e.g., from Molecular Probes).

Bioluminescence-Based Moieties. The subjects of chemiluminescence (luminescence as a result of a chemical reaction) and bioluminescence (visible luminescence from living organisms) have, in many aspects, been thoroughly studied (e.g., Campbell, 1988, *Chemiluminescence. Principles and Applications in Biology and Medicine* (Chichester, England: Ellis Horwood Ltd. and VCH Verlagsgesellschaft mbH)). A brief summary of salient features follows.

Bioluminescent molecules are distinguished from fluorescent molecules in that they do not require the input of radiative energy to emit light. Rather, bioluminescent molecules utilize chemical energy, such as ATP, to produce light. An advantage of bioluminescent moieties, as opposed to fluorescent moieties, is that there is virtually no background in the signal. The only light detected is light that is produced by the exogenous bioluminescent moiety. In contrast, the light used to excite a fluorescent molecule often results in the fluorescence of substances other than the intended target. This is particularly true when the "background" is as complex as the internal environment of a living animal.

Several types of bioluminescent molecules are known. They include the luciferase family (e.g., Wood, et al., 1989, *Science* 244:700–702) and the aequorin family (e.g., Prasher, et al., *Biochem.* 26:1326–1332). Members of the luciferase family have been identified in a variety of prokaryotic and eukaryotic organisms. Luciferase and other enzymes involved in the prokaryotic luminescent (lux) systems, as well as the corresponding lux genes, have been isolated from marine bacteria in the *Vibrio* and *Photobacterium* genera and from terrestrial bacteria in the *Xenorhabdus* genus.

An exemplary eukaryotic organism containing a luciferase system (luc) is the North American firefly *Photinus pyralis*. Firefly luciferase has been extensively studied, and is widely used in ATP assays. cDNAs encoding luciferases from *Pyrophorus plagiophthalamus*, another species of click beetle, have been cloned and expressed (Wood, et al., 1989, *Science* 244:700–702). This beetle is unusual in that different members of the species emit bioluminescence of different colors. Four classes of clones, having 95–99% homology with each other, were isolated. They emit light at 546 nm (green), 560 nm (yellow-green), 578 nm (yellow) and 593 nm (orange). The last class (593 nm) may be particularly advantageous for use as a light-generating moiety with the present invention, because the emitted light has a wavelength that penetrates tissues more easily than shorter wavelength light.

Luciferases, as well as aequorin-like molecules, require a source of energy, such as ATP, NAD(P)H, and the like, and a substrate, such as luciferin or coelentrizine and oxygen.

The substrate luciferin must be supplied to the luciferase enzyme in order for it to luminesce. In those cases where a luciferase enzyme is introduced as an expression product of a vector containing cDNA encoding a lux luciferase, a convenient method for providing luciferin is to express not only the luciferase but also the biosynthetic enzymes for the synthesis of luciferin. In cells transformed with such a construct, oxygen is the only extrinsic requirement for bioluminescence. Such an approach, detailed in Example 1, is employed to generate lux-transformed *Salmonella*, which are used in experiments performed in support of the present invention and detailed herein.

The plasmid construct, encoding the lux operon obtained from the soil bacterium *Xenorhabdus luminescens* (Frackman, et al., 1990, *J. Bact.* 172:5767–5773), confers on transformed *E coli* the ability to emit photons through the expression of the two subunits of the heterodimeric luciferase and three accessory proteins (Frackman, et al., 1990). Optimal bioluminescence for *E. Coli* expressing the lux genes of *X. luminescens* is observed at 37° C. (Szittner and Meighen, 1990, *J. Biol. Chem.* 265:16581–16587, Xi, et al., 1991, *J. Bact.* 173:1399–1405) in contrast to the low temperature optima of luciferases from eukaryotic and other prokaryotic luminescent organisms (Campbell, 1988, *Chemiluminescence. Principles and Applications in Biology and Medicine* (Chichester, England: Ellis Horwood Ltd. and VCH Verlagsgesellschaft mbH)). The luciferase from *X.*

*luminescens*, therefore, is well-suited for use as a marker for studies in animals.

Luciferase vector constructs such as the one described above and in Example 1, can be adapted for use in transforming a variety of host cells, including most bacteria, and many eukaryotic cells (luc constructs). In addition, certain viruses, such as herpes virus and vaccinia virus, can be genetically-engineered to express luciferase. For example, Kovacs Sz. and Mettenlieter, 1991, *J. Gen. Virol.* 72:2999–3008, teach the stable expression of the gene encoding firefly luciferase in a herpes virus. Brasier and Ron, 1992, *Meth. in Enzymol.* 216:386–396, teach the use of luciferase gene constructs in mammalian cells. Luciferase expression from mammalian cells in culture has been studied using CCD imaging both macroscopically (Israel and Honigman, 1991, *Gene* 104:139–145) and microscopically (Hooper, et al., 1990, *J. Biolum. and Chemilum.* 5:123–130).

2. Entities

The invention includes entities which have been modified or conjugated to include a light-generating moiety, construct or molecule, such as described above. Such conjugated or modified entities are referred to as light-emitting entities, light-emitting conjugates (LECs) or simply conjugates. The entities themselves may take the form of, for example, molecules, macromolecules, particles, microorganisms, or cells. The methods used to conjugate a light-generating moiety to an entity depend on the nature of the moiety and the entity. Exemplary conjugation methods are discussed in the context of the entities described below.

Small molecules. Small molecule entities which may be useful in the practice of the present invention include compounds which specifically interact with a pathogen or an endogenous ligand or receptor. Examples of such molecules include, but are not limited to, drugs or therapeutic compounds; toxins, such as those present in the venoms of poisonous organisms, including certain species of spiders, snakes, scorpions, dinoflagellates, marine snails and bacteria; growth factors, such as NGF, PDGF, TGF and TNF; cytokines; and bioactive peptides.

The small molecules are preferably conjugated to light-generating moieties that interfere only minimally, if at all, with the bioactivity of the small molecule, such as small fluorescent molecules (described above). Conjugations are typically chemical in nature, and can be performed by any of a variety of methods known to those skilled in the art.

The small molecule entity may be synthesized to contain a light-generating moiety, so that no formal conjugation procedure is necessary. Alternatively, the small molecule entity may be synthesized with a reactive group that can react with the light generating moiety, or vice versa.

Small molecules conjugated to light-generating moieties of the present invention may be used either in animal models of human conditions or diseases, or directly in human subjects to be treated. For example, a small molecule which binds with high affinity to receptor expressed on tumor cells may be used in an animal model to localize and obtain size estimates of tumors, and to monitor changes in tumor growth or metastasis following treatment with a putative therapeutic agent. Such molecules may also be used to monitor tumor characteristics, as described above, in cancer patients.

Macromolecules. Macromolecules, such as polymers and biopolymers, constitute another example of entities useful in practicing the present invention. Exemplary macromolecules include antibodies, antibody fragments, fusion proteins and certain vector constructs.

Antibodies or antibody fragments, purchased from commercial sources or made by methods known in the art (Harlow, et al., 1988, *Antibodies: A Laboratory Manual*, Chapter 10, pg. 402, Cold Spring Harbor Press), can be used to localize their antigen in a mammalian subject by conjugating the antibodies to a light-generating moiety, administering the conjugate to a subject by, for example, injection, allowing the conjugate to localize to the site of the antigen, and imaging the conjugate.

Antibodies and antibody fragments have several advantages for use as entities in the present invention. By their nature, they constitute their own targeting moieties. Further, their size makes them amenable to conjugation with several types of light-generating moieties, including small fluorescent molecules and fluorescent and bioluminescent proteins, yet allows them to diffuse rapidly relative to, for example, cells or liposomes.

The light-generating moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., 1990, *PNAS* 87:2047–2051, describe a method of making a vector construct capable of expressing a fusion protein of aequorin and an antibody gene in mammalian cells.

Conjugates containing antibodies can be used in a number of applications of the present invention. For example, a labeled antibody directed against E-selectin, which is expressed at sites of inflammation, can be used to localize the inflammation and to monitor the effects of putative anti-inflammatory agents.

Vector constructs by themselves can also constitute macromolecular entities applicable to the present invention. For example, a eukaryotic expression vector can be constructed which contains a therapeutic gene and a gene encoding a light-generating molecule under the control of a selected promoter (i.e., a promoter which is expressed in the cells targeted by the therapeutic gene). Expression of the light-generating molecule, assayed using methods of the present invention, can be used to determine the location and level of expression of the therapeutic gene. This approach may be particularly useful in cases where the expression of the therapeutic gene has no immediate phenotype in the treated individual or animal model.

Viruses. Another entity useful for certain aspects of the invention are viruses. As many viruses are pathogens which infect mammalian hosts, the viruses may be conjugated to a light-generating moiety and used to study the initial site and spread of infection. In addition, viruses labeled with a light-generating moiety may be used to screen for drugs which inhibit the infection or the spread of infection.

A virus may be labeled indirectly, either with an antibody conjugated to a light-generating moiety, or by, for example, biotinylating virions (e.g., by the method of Dhawan, et al., 1991, *J. Immunol.* 147(1):102) and then exposing them to streptavidin linked to a detectable moiety, such as a fluorescent molecule.

Alternatively, virions may be labeled directly with a fluorophore like rhodamine, using, for example, the methods of Fan, et al., 1992, *J. Clin. Micro.* 30(4):905. The virus can also be genetically engineered to express a light-generating protein. The genomes of certain viruses, such as herpes and vaccinia, are large enough to accommodate genes as large as the lux or luc genes used in experiments performed in support of the present invention.

Labeled virus can be used in animal models to localize and monitor the progression of infection, as well as to screen for drugs effective to inhibit the spread of infection. For example, while herpes virus infections are manifested as skin lesions, this virus can also cause herpes encephalitis. Such an infection can be localized and monitored using a virus labeled by any of the methods described above, and various antiviral agents can be tested for efficacy in central nervous system (CNS) infections.

Particles. Particles, including beads, liposomes and the like, constitute another entity useful in the practice of the present invention. Due to their larger size, particles may be conjugated with a larger number of light-generating molecules than, for example, can small molecules. This results in a higher concentration of light emission, which can be detected using shorter exposures or through thicker layers of tissue. In addition, liposomes can be constructed to contain an essentially pure targeting moiety, or ligand, such as an antigen or an antibody, on their surface. Further, the liposomes may be loaded with, for example, bioluminescent protein molecules, to relatively high concentrations (Campbell, 1988, *Chemiluminescence. Principles and Applications in Biology and Medicine* (Chichester, England: Ellis Horwood Ltd. and VCH Verlagsgesellschaft mbH)).

Furthermore, two types of liposomes may be targeted to the same cell type such that light is generated only when both are present. For example, one liposome may carry luciferase, while the other carries luciferin. The liposomes may carry targeting moieties, and the targeting moieties on the two liposomes may be the same or different. Viral proteins on infected cells can be used to identify infected tissues or organs. Cells of the immune system can be localized using a single or multiple cell surface markers.

The liposomes are preferably surface-coated, e.g., by incorporation of phospholipid—polyethyleneglycol conjugates, to extend blood circulation time and allow for greater targeting via the bloodstream. Liposomes of this type are well known.

Cells. Cells, both prokaryotic and eukaryotic, constitute another entity useful in the practice of the present invention. Like particles, cells can be loaded with relatively high concentrations of light-generating moieties, but have the advantage that the light-generating moieties can be provided by, for example, a heterologous genetic construct used to transfect the cells. In addition, cells can be selected that express "targeting moieties", or molecules effective to target them to desired locations within the subject. Alternatively, the cells can be transfected with a vector construct expressing an appropriate targeting moiety.

The cell type used depends on the application. For example, as is detailed below, bacterial cells, such as *Salmonella*, can be used to study the infective process, and to evaluate the effects of drugs or therapeutic agents on the infective process with a high level of temporal and spatial resolution.

Bacterial cells constitute effective entities. For example, they can be easily transfected to express a high levels of a light-generating moiety, as well as high levels of a targeting protein. In addition, it is possible to obtain *E. coli* libraries containing bacteria expressing surface-bound antibodies which can be screened to identify a colony expressing an antibody against a selected antigen (Stratagene, La Jolla, Calif.). Bacteria from this colony can then be transformed with a second plasmid containing a gene for a light-generating protein, and transformants can be utilized in the methods of the present invention, as described above, to localize the antigen in a mammalian host.

Pathogenic bacteria can be conjugated to a light-generating moiety and used in an animal model to follow the infection process in vivo and to evaluate potential anti-infective drugs, such as new antibiotics, for their efficacy in inhibiting the infection. An example of this application is illustrated by experiments performed in support of the present invention and detailed below.

Eukaryotic cells are also useful as entities in aspects of the present invention. Appropriate expression vectors, containing desired regulatory elements, are commercially available. The vectors can be used to generate constructs capable of expressing desired light-generating proteins in a variety of eukaryotic cells, including primary culture cells, somatic cells, lymphatic cells, etc. The cells can be used in transient expression studies, or, in the case of cell lines, can be selected for stable transformants.

Expression of the light-generating protein in transformed cells can be regulated using any of a variety of selected promoters. For example, if the cells are to be used as light-emitting entities targeted to a site in the subject by an expressed ligand or receptor, a constitutively-active promoter, such as the CMV or SV40 promoter may be used. Cells transformed with such a construct can also be used to assay for compounds that inhibit light generation, for example, by killing the cells.

Alternatively, the transformed cells may be administered such they become uniformly distributed in the subject, and express the light-generating protein only under certain conditions, such as upon infection by a virus or stimulation by a cytokine. Promoters that respond to factors associated with these and other stimuli are known in the art. In a related aspect, inducible promoters, such as the Tet system (Gossen and Bujard, 1992, *PNAS* 89:5547–5551) can be used to transiently activate expression of the light-generating protein.

For example, CD4+ lymphatic cells can be transformed with a construct containing tat-responsive HIV LTR elements, and used as an assay for infection by HIV (Israel and Honigman, 1991, *Gene* 104:139–145). Cells transformed with such a construct can be introduced into SCID-hu mice (McCune, et al., 1988, *Science* 241:1632–1639) and used as model for human HIV infection and AIDS.

Tumor cell lines transformed as above, for example, with a constitutively-active promoter, may be used to monitor the growth and metastasis of tumors. Transformed tumor cells may be injected into an animal model, allowed to form a tumor mass, and the size and metastasis of the tumor mass monitored during treatment with putative growth or metastasis inhibitors.

Tumor cells may also be generated from cells transformed with constructs containing regulatable promoters, whose activity is sensitive to various infective agents, or to therapeutic compounds.

Cell Transformation. Transformation methods for both prokaryotic cells and eukaryotic cells are well known in the art (Sambrook, et al., 1989, In *Molecular Cloning: A Laboratory Manual*, Cold Spring Harbor Laboratory Press, Vol. 2). Vectors containing the appropriate regulatory elements and multiple cloning sites are widely commercially available (e.g., Stratagene, La Jolla, Calif., Clontech, Palo Alto, Calif.).

D. Transgenic Animals Containing Genes Encoding Light-Generating Proteins

In another aspect, the present invention includes transgenic animals containing a heterologous gene construct encoding a light-generating protein or complex of proteins. The construct is driven by a selected promoter, and can include, for example, various accessory proteins required for the functional expression of the light-generating protein, as well as selection markers and enhancer elements.

Activation of the promoter results in increased expression of the genes encoding the light-generating molecules and accessory proteins. Activation of the promoter is achieved by the interaction of a selected biocompatible entity, or parts of the entity, with the promoter elements. If the activation occurs only in a part of the animal, only cells in that part will express the light-generating protein.

For example, an interferon-inducible promoter, such as the promoter for 3'-5' poly-A synthetase or the Mx protein (an interferon-inducible promoter), can be used to detect the infection of transgenic cells by a number of different RNA viruses.

In a related aspect, a promoter expressed in certain disease states can be used to mark affected areas in a transgenic animal, and expression of the light-generating moiety can be used to monitor the effects of treatments for the disease state. For example, E-selectin is expressed at sites of inflammation in vivo (Pober and Cotran, 1991, Lab. Invest. 64:301–305). Accordingly, the E-selectin promoter can be isolated and used to drive the expression of a luciferase gene.

It is also possible to use methods of the invention with tissue-specific promoters. This enables, for example, the screening of compounds which are effective to inhibit pathogenic processes resulting in the degeneration of a particular organ or tissue in the body, and permits the tracking of cells (e.g., neurons) in, for example, a developing animal.

Many promoters which are applicable for use with the present invention are known in the art. In addition, methods are known for isolating promoters of cloned genes, using information from the gene's cDNA to isolate promoter-containing genomic DNA.

In a specific embodiment of the present invention, transgenic animals expressing luciferase under the control of the HIV-1 LTR have been generated. As demonstrated in specific examples, luciferase expression serves as a real-time bioluminescent reporter which allows the noninvasive assessment of the level of promoter activity in vivo. As described, supra, the photons from the in vivo luciferase reaction can be detected by a CCD camera, after transmission through animal tissues, and used as an indication of the level and location of gene expression both in superficial and internal tissues.

E. Imaging of Light-Emitting Conjugates

Light emitting conjugates that have localized to their intended sites in a subject may be imaged in a number of ways. Guidelines for such imaging, as well as specific examples, are described below.

1. Localization of Light-Emitting Conjugates

In the case of "targeted" entities, that is, entities which contain a targeting moiety—a molecule or feature designed to localize the entity within a subject or animal at a particular site or sites, localization refers to a state when an equilibrium between bound, "localized", and unbound, "free" entities within a subject has been essentially achieved. The rate at which such an equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization.

Alternatively, localization may simply refer to the location of the entity within the subject or animal at selected time periods after the entity is administered. For example, in experiments detailed herein, *Salmonella* are administered (e.g., orally) and their spread is followed as a function of time. In this case, the entity can be "localized" immediately following the oral introduction, inasmuch as it marks the initial location of the administered bacteria, and its subsequent spread or recession (also "localization") may be followed by imaging.

In a related aspect, localization of, for example, injected tumors cells expressing a light-generating moiety, may consist of the cells colonizing a site within the animal and forming a tumor mass.

By way of another example, localization is achieved when an entity becomes distributed following administration. For example, in the case of a conjugate administered to measure the oxygen concentration in various organs throughout the subject or animal, the conjugate becomes "localized", or informative, when it has achieved an essentially steady-state of distribution in the subject or animal.

In all of the above cases, a reasonable estimate of the time to achieve localization may be made by one skilled in the art. Furthermore, the state of localization as a function of time may be followed by imaging the light-emitting conjugate according to the methods of the invention.

2. Photodetector Devices

An important aspect of the present invention is the selection of a photodetector device with a high enough sensitivity to enable the imaging of faint light from within a mammal in a reasonable amount of time, preferably less than about 30 minutes, and to use the signal from such a device to construct an image.

In cases where it is possible to use light-generating moieties which are extremely bright, and/or to detect light-emitting conjugates localized near the surface of the subject or animal being imaged, a pair of "night-vision" goggles or a standard high-sensitivity video camera, such as a Silicon Intensified Tube (SIT) camera (e.g., Hamamatsu Photonic Systems, Bridgewater, N.J.), may be used. More typically, however, a more sensitive method of light detection is required.

In extremely low light levels, such as those encountered in the practice of the present invention, the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon.

By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor.

Reduced-Noise Photodetection Devices. The first class constitutes devices which achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. The "backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

Photon Amplification Devices. A second class of sensitive photodetectors includes devices which amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification.

An exemplary microchannel intensifier-based single-photon detection device is the C2400 series, available from Hamamatsu.

Image Processors. Signals generated by photodetector devices which count photons need to be processed by an image processor in order to construct an image which can be, for example, displayed on a monitor or printed on a video printer. Such image processors are typically sold as part of systems which include the sensitive photon-counting cameras described above, and accordingly, are available from the same sources (e.g., Photometrics, Ltd., and Hamamatsu). Image processors from other vendors can also be used, but more effort is generally required to achieve a functional system.

The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

3. Immobilizing Subject in Detection Field of Device

Detection Field Of Device. The detection field of the device is defined as the area from which consistent measurements of photon emission can be obtained. In the case of a camera using an optical lens, the detection field is simply the field of view accorded to the camera by the lens. Similarly, if the photodetector device is a pair of "night vision" goggles, the detection field is the field of view of the goggles.

Alternatively, the detection field may be a surface defined by the ends of fiber-optic cables arranged in a tightly-packed array. The array is constructed to maximize the area covered by the ends of the cables, as opposed to void space between cables, and placed in close proximity to the subject. For instance, a clear material such as plexiglass can be placed adjacent the subject, and the array fastened adjacent the clear material, opposite from the subject.

The fiber-optic cable ends opposite the array can be connected directly to the detection or intensifying device, such as the input end of a microchannel intensifier, eliminating the need for a lens.

An advantage of this method is that scattering and/or loss of photons is reduced by eliminating a large part of the air space between the subject and the detector, and/or by eliminating the lens. Even a high-transmission lens, such as the 60 mm AF Nikkor macro lens used in experiments performed in support of the present invention, transmits only a fraction of the light reaching the front lens element.

With higher-intensity LGMs, photodiode arrays may be used to measure photon emission. A photodiode array can be incorporated into a relatively flexible sheet, enabling the practitioner to partially "wrap" the array around the subject. This approach also minimizes photon loss, and in addition, provides a means of obtaining three-dimensional images of the bioluminescence.

Other approaches may be used to generate three-dimensional images, including multiple detectors placed around the subject or a scanning detector or detectors.

It will be understood that the entire animal or subject need not necessarily be in the detection field of the photodetection device. For example, if one is measuring a light-emitting conjugate known to be localized in a particular region of the subject, only light from that region, and a sufficient surrounding "dark" zone, need be measured to obtain the desired information.

Immobilizing The Subject. In those cases where it is desired to generate a two-dimensional or three-dimensional image of the subject, the subject may be immobilized in the detection field of the photodetection devices during the period that photon emission is being measured. If the signal is sufficiently bright that an image can be constructed from photon emission measured in less than about 20 milliseconds, and the subject is not particularly agitated, no special immobilization precautions may be required, except to insure that the subject is in the field of the detection device at the start of the measuring period.

If, on the other hand, the photon emission measurement takes longer than about 20 msec, and the subject is agitated, precautions to insure immobilization of the subject during photon emission measurement, commensurate with the degree of agitation of the subject, need to be considered to preserve the spatial information in the constructed image. For example, in a case where the subject is a person and photon emission measurement time is on the order of a few seconds, the subject may simply be asked to remain as still as possible during photon emission measurement (imaging). On the other hand, if the subject is an animal, such as a mouse, the subject can be immobilized using, for example, an anesthetic or a mechanical restraining device.

A variety of restraining devices may be constructed. For example, a restraining device effective to immobilize a mouse for tens of seconds to minutes may be built by fastening a plexiglass sheet over a foam cushion. The cushion has an indentation for the animal's head at one end. The animal is placed under the plexiglass such that its head is over the indentation, allowing it to breathe freely, yet the movement of its body is constrained by the foam cushion.

In cases where it is desired to measure only the total amount of light emanating from a subject or animal, the subject does not necessarily need to be immobilized, even for long periods of photon emission measurements. All that is required is that the subject be confined to the detection field of the photodetector during imaging. It will be appreciated, however, that immobilizing the subject during such measuring may improve the consistency of results obtained, because the thickness of tissue through which detected photons pass will be more uniform from animal to animal.

4. Further Considerations During Imaging

Fluorescent Light-Generating Moieties. The visualization of fluorescent light-generating moieties requires an excitation light source, as well as a photodetector. Furthermore, it will be understood that the excitation light source is turned on during the measuring of photon emission from the light-generating moiety.

Appropriate selection of a fluorophore, placement of the light source and selection and placement of filters, all of which facilitate the construction of an informative image, are discussed above, in the section on fluorescent light-generating moieties.

High-Resolution Imaging. Photon scattering by tissue limits the resolution that can be obtained by imaging LGMs through a measurement of total photon emission. It will be understood that the present invention also includes embodiments in which the light-generation of LGMs is synchronized to an external source which can be focused at selected points within the subject, but which does not scatter significantly in tissue, allowing the construction of higher-resolution images. For example, a focused ultrasound signal can be used to scan, in three dimensions, the subject being imaged. Light-generation from areas which are in the focal point of the ultrasound can be resolved from other photon emission by a characteristic oscillation imparted to the light by the ultrasound (e.g., Houston and Moerner, U.S. Pat. No. 4,614,116, issued 30, Sep. 1986.)

5. Constructing an Image of Photon Emission

In cases where, due to an exceptionally bright light-generating moiety and/or localization of light-emitting conjugates near the surface of the subject, a pair of "night-vision" goggles or a high sensitivity video camera was used to obtain an image, the image is simply viewed or displayed on a video monitor. If desired, the signal from a video camera can be diverted through an image processor, which can store individual video frames in memory for analysis or printing, and/or can digitize the images for analysis and printing on a computer.

Alternatively, if a photon counting approach is used, the measurement of photon emission generates an array of numbers, representing the number of photons detected at each pixel location, in the image processor. These numbers are used to generate an image, typically by normalizing the photon counts (either to a fixed, pre-selected value, or to the maximum number detected in any pixel) and converting the normalized number to a brightness (greyscale) or to a color (pseudocolor) that is displayed on a monitor. In a pseudocolor representation, typical color assignments are as follows. Pixels with zero photon counts are assigned black, low counts blue, and increasing counts colors of increasing wavelength, on up to red for the highest photon count values. The location of colors on the monitor represents the distribution of photon emission, and, accordingly, the location of light-emitting conjugates.

In order to provide a frame of reference for the conjugates, a greyscale image of the (still immobilized) subject from which photon emission was measured is typically constructed. Such an image may be constructed, for example, by opening a door to the imaging chamber, or box, in dim room light, and measuring reflected photons (typically for a fraction of the time it takes to measure photon emission). The greyscale image may be constructed either before measuring photon emission, or after.

The image of photon emission is typically superimposed on the greyscale image to produce a composite image of photon emission in relation to the subject.

If it desired to follow the localization and/or the signal from a light-emitting conjugate over time, for example, to record the effects of a treatment on the distribution and/or localization of a selected biocompatible moiety, the measurement of photon emission, or imaging can be repeated at selected time intervals to construct a series of images. The intervals can be as short as minutes, or as long as days or weeks.

F. Analysis of Photon Emission Images

Images generated by methods and/or using compositions of the present invention may be analyzed by a variety of methods. They range from a simple visual examination, mental evaluation and/or printing of a hardcopy, to sophisticated digital image analysis. Interpretation of the information obtained from an analysis depends on the phenomenon under observation and the entity being used.

The following experiments illustrate one application of the present invention—tracking *Salmonella* infection in live mice—and how images obtained using methods of the present invention can be analyzed. Similarly, infection of numerous other pathogens, including, but not limited to, *Pseudomonas, Staphylococcus, Streptococcus, Enterococcus, Enterobacter, Citrobacter, Leginella, Helicobacter, Acinetobacter, Escherichia, Klebsiella* and *Serratia*.

G. Imaging of Luminescent *Salmonella* in Living Mice

Experiments performed in support of the present invention characterize the distribution of *Salmonella typhimurium* infection in mice, the animal model of human typhoid. A mouse virulent *Salmonella typhimurium* strain, SL1344 (Hoiseth and Stocker, 1981, *Nature* 291:238–239), a non-invasive mutant of SL1344, BJ66 and a low virulence LT-2 strain of *Salmonella*, LB5000 were each marked with a plasmid containing the lux operon, and used in experiments to localize *Salmonella* infection in mice.

1. Constructions of Luminescent *Salmonella*

*Salmonella* Strains. Three strains of *Salmonella typhimurium* with differing virulence phenotypes, defined by oral and intra-peritoneal inoculations into mice, are selected for transformation.

The most virulent phenotype used herein is SL1344, a mouse strain originally obtained from a fatal infection of a calf (Hoiseth and Stocker, 1981, *Nature* 291:238–239). Following oral inoculations of mice with this strain, bacteria are disseminated systematically via the lymphatic system resulting in colonization of the liver, spleen and bone marrow (Carter and Collins, 1974, *J. Exper. Med.* 139:1189–1203.; see also reviews by Finlay and Falkow, 1989, *Mol. Microbiol.* 3:1833–1841, and Hsu, 1989, *Microbiol. Rev.* 53:390–409.)

A non-invasive mutant of SL1344, BJ66, is also evaluated. Systemic infections in mice do not typically result from, an oral inoculation with BJ66, but do result from intraperitoneal inoculations with this strain.

A low virulence LT-2 strain of *Salmonella*, LB5000, is also examined. LT-2 stains are laboratory strains known to be of reduced or variable virulence for mice. LB5000 contains multiple auxotrophic mutations, is streptomycin resistant, and is cleared from mice following oral or intra-peritoneal inoculations.

Transformation of *Salmonella* Strains with the lux Operon. The three strains are each transformed with a plasmid encoding the lux operon, as detailed in Example 1. The plasmid, obtained from the soil bacterium *Xenorhabdus luminescens* (Frackman, et al., 1990) confers on *E coli* the ability to emit photons through the expression of the two subunits of the heterodimeric luciferase and three accessory proteins, luxC, luxD and luxE.

Inclusion of luxC, luxD and luxE removes the necessity of providing the fatty aldehyde substrate, luciferin, to the luciferase-expressing cells. Because supplying the substrate to eukaryotic luciferase enzymes in an in vivo system such as described herein may prove difficult, the entire lux operon of *X. luminescens* is used. The operon also encodes the enzymes for the biosynthesis of the fatty aldehyde substrate.

*X. luminescens* luciferase, an alpha-beta heterodimeric mixed-function oxidase, catalyzes the oxidation of reduced flavin and long-chain aldehyde to oxidized flavin and the corresponding long-chain fatty acid. A fatty acid reductase complex is required for the generation and recycling of fatty acid to aldehyde, and an NAD(P)H:flavin oxidoreductase supplies the reduced flavin.

Optimal bioluminescence for *E. Coli* expressing the lux genes of *X. luminescens* is 37° C. (Szittner and Meighen, 1990, *J. Biol. Chem.* 265:16581–16587, Xi, et al., 1991, *J. Bact.* 173:1399–1405). In contrast, luciferases from eukaryotic and other prokaryotic luminescent organisms typically have lower temperature optima (Campbell, 1988, *Chemiluminescence. Principles and Applications in Biology and Medicine* (Chichester, England: Ellis Horwood Ltd. and VCH Verlagsgesellschaft mbH)). The luciferase from *X. luminescens*, therefore, is well-suited for use as a marker for studies in animals.

The three strains are transformed by electroporation with the plasmid pGSL1, which contains the entire *X. luminescens* lux operon and confers resistance to ampicillin and carbenicillin on the *Salmonella* (Frackman, et al., 1990). The *X. luminescens* lux operon contains the genes luxA, luxb, luxC, luxD and luxE (Frackman, et al., 1990). LuxA and B encode the two subunits of the heterodimeric luciferase. luxC and D encode the biosynthetic enzymes for the luciferase substrate and luxE is a regulatory gene. Inclusion of the genes for the biosynthesis of the substrate is a convenient means of providing substrate to luciferase, in contrast to supplying luciferin externally to the cells in culture or treating animals with the substrate.

2. Characterization of Transformed *Salmonella* in Vitro

Adherence And Invasive Properties. The adherence and invasive properties of the three *Salmonella* strains containing the lux plasmid are compared in culture, to each other, and to their non-luminescent parental strains by the standard invasion assay as described by Finlay and Falkow, 1989, *Mol. Microbiol.* 3:1833–1841., and detailed in Example 2.

In this assay, adherent and intracellular bacteria are quantified following incubation with an epithelial cell line and peritoneal macrophages. The adherent and intracellular bacteria are detected and quantified by both the emission of photons from living cells, and colony forming units following lysis and plating the cell lysates on carbenicillin-containing plates.

The results of some of the assays are shown in FIGS. 2A through 2E and discussed in Example 8. The phenotypes of the three strains transformed with the lux expressing plasmid are not significantly altered in comparison to the parental *Salmonella* strains. In addition, there is a good correlation between the intensity of bioluminescence and the CFU from the HEp-2 cells and macrophages. The results show that luminescence, as an indicator of intracellular bacteria, is a rapid method for assaying the invasive properties of bacteria in culture.

BJ66 demonstrated reduced adherence to HEp-2 cells in comparison to SL1344, however, adherence of the two strains in primary cultures of murine peritoneal macrophages were comparable.

Light Emission. To evaluate the oxygen requirements of the system, 10 fold serial dilutions of bacteria are placed in glass capillary tubes and imaged, as detailed in Example 3.

FIG. 3 shows an image generated in one such experiment. Luminescence is only detected at the air-liquid interface, even in the tubes with small numbers of bacteria in air saturated medium (0.1 ml of air saturated buffer in 5 l results in a final $O_2$ concentration of 5 nM).

From these results, it is apparent that oxygen is likely a limiting factor for luminescence.

Light Transmission Through Animal Tissue. To determine the degree to which light penetrates animal tissue, light emitted from luminescent *Salmonella* and transmitted through tissue is quantified using a scintillation counter, with the fast coincidence detector turned off to detect single photons. The background due to dark current of the photomultiplier tubes in this type of detection is significant, limiting the assay to samples with relatively strong photon emission.

Four tissue types of varying opacity are compared using this approach: muscle from chicken breast, skin from chicken breast, lamb kidney and renal medulla from lamb kidney. The number of photons that can be detected through tissue is approximately ten fold less than the controls without tissue.

3. Characterization of Lux *Salmonella* in vivo

Oral Administration. Oral inoculation is natural route of infection of mice or humans with *Salmonella* and results in a more protracted course of disease. In order to study the progression of the *Salmonella* infection following this route of inoculation, two strains of mice are infected with the three strains of *Salmonella*. The results obtained using the resistant animals are discussed under the heading "Infection of Resistant Mice", below.

Balb/c mice are orally infected with suspensions of virulent SL1344lux, non-invasive BJ66lux and low virulence LB5000lux *Salmonella*, as described in Example 5. Progression of the infection is followed by external imaging (Materials and Methods) over an 8 day period.

Representative images are shown in FIGS. 6A, 6B, and 6C. At 24 hours post inoculation (p.i.), the bioluminescent signal is localized at a single focus in all infected animals (FIGS. 6A, 6B and 6C). Bioluminescence disappears in all animals infected with the low virulence LB5000lux by 7 days p.i. (FIG. 6A). Animals infected with the virulent SL1344lux, on the other hand, show virulent infection which often spreads over much of the abdominal cavity (FIG. 6C), though the time at which it begins to spread is highly variable from animal to animal. The infection by BJ66lux typically persists and remains localized at a single site (FIG. 6B).

I.P. Inoculation. To assess whether or not there is sufficient $O_2$ at the sites of *Salmonella* replication for the oxidation of luciferin and subsequent luminescence (Campbell, 1988, *Chemiluminescence. Principles and Applications in Biology and Medicine* (Chichester, England: Ellis Horwood Ltd. and VCH Verlagsgesellschaft mbH)), photon emission is measured from the tissues of a respiring animal. Luminescent SL1344lux and LB5000lux are inoculated into the peritoneal cavities of two groups of Balb/c mice. 32 hours post inoculation (p.i.), the transmitted photons are imaged (FIG. 7).

In the mice infected with SL1344lux (left part of FIGURE), transmitted photons are evident over a large surface, with foci of varying intensities visible. These images are indicative of a disseminated infection, and are consistent with widespread colonization of the viscera, possibly including the liver and mesenteric lymph nodes. In contrast, the distributions of transmitted photons from animals infected with the LB5000lux strain is very limited, indicating a limited infection.

The LB5000lux-infected mice remained healthy for several weeks p.i., while the SL1344lux-infected mice were nearly moribund and euthanized at 4 days p.i.

These experiments indicate that the level of $O_2$ in the blood and or tissues is adequate for bioluminescence of lux luciferase expressed by *Salmonella*. Furthermore, the experiments are consistent with the invasive nature of the virulent strain SL1344 in comparison to the reduced virulent laboratory strain LB5000.

Infection Of Resistant Mice. Mice which are heterozygous at the Ity locus ($Ity^{r/s}$) are resistant to systemic infections by *S. typhimurium* (Plant and Glynn, 1976, *J. Infect. Dis.* 133:72–78). This locus, also called Bcg (Gros, et al., 1981, *J Immunol.* 127:2417–2421) or Lsh (Bradley, 1977, *Clin. and Exper. Immunol.* 30:130–140), regulates the pathogenic processes of certain intracellular pathogens, such as *Mycobacterium lepraemurium* (Forget, et al., 1981, *Infect. Immunol.* 32:42–47), *M. Bovis* (Skamene, et al., 1984, *Immunogenet.* 19:117–120, Skamene and Pietrangeli, 1991, *Nature* 297:506–509) and *M. intracelluare* (Goto, et al., 1989, *Immunogenetics* 30:218–221). An analogous genetic control of resistance and susceptibility to intracellular pathogens appears to be in humans as well (*M. tuberculosis* (Stead, 1992, *Annals of Intern. Med.* 116:937–941, Stead, et al., et al., 1990, *New Eng. J. Med.* 322:422–427) and *M. leprae*).

The Ity locus is located on mouse chromosome 1 with two allelic forms, $Ity^r$ (resistant, dominant) and $Ity^s$ (sensitive, recessive). The gene encoded at the Ity locus apparently affects the ability of macrophages to disrupt the internalized pathogens (reviewed by Blackwell, et al., 1991, *Immunol. Lett.* 30:241–248 (1991); see also Skamene, et al., 1984, *Immunogenet.* 19:117–120, Skamene and Pietrangeli, 1991, *Nature* 297:506–509) which in turn, affects the down stream function of the proposed macrophage-mediated transport of pathogens to other sites within the infected host. Balb/c mice are $Ity^{s/s}$ and 129 mice are $Ity^{r/r}$. The heterozygous Balb/c× 129 mice ($Ity^{r/s}$) are used in experiments detailed herein.

Resistant 129×Balb/c ($Ity^{r/s}$) viable mice are infected by intragastric inoculation of $1 \times 10^7$ SL1344lux *Salmonella* as detailed in Example 7. The animals are imaged daily for 8 days post injection (d.p.i.).

Results are shown in FIGS. 8A (day 1) and 8B (day 8). The luminescence, detected by external imaging, is apparent at 24 h p.i., and appeared to localized to a single site in all animals. The luminescent signal is present throughout the study period (up to 8 days p.i.). The intensity of the luminescence and the location of the luminescent source is somewhat variable over time within a mouse and also from mouse to mouse. The luminescent tissue in all infected animals is the cecum (see below) and the variability in localization, and possibly intensity, is most likely due fact that internal organs of rodents are not tightly fixed in position.

The apparent limited infection observed in these animals supports the interpretation that the Ity restriction blocks macrophage transport. The persistence of this infection for 10 days, however, suggests that there is adherence to the intestine mucosa and prolonged shedding of bacteria in the feces of these animals, as evidenced by luminescent fecal pellets. These results indicate that the luminescent phenotype of the *Salmonella* in vivo is retained over an 8 day duration in Ity restricted animals and that localization is possible following an oral inoculation.

Internal Imaging Following Oral Inoculation. In order to further localize the luminescent signal in the abdominal cavity, infected mice are imaged following laparotomy (Example 8). The predominant disease manifestation in all of the animals infected by the oral route is an enlarged cecum (FIGS. 9A, 9B, 9C). The "external" image (FIG. 9A) illustrates a focal luminescence, which is revealed in the post-laparotomy image (FIG. 9B) to be the cecum.

Injection of air into the intestine confirms the presence of bacteria in other regions of the digestive tract. Bacteria in the colon and rectum are likely expressing luciferase, but low oxygen concentrations are likely limiting light emission from these sites.

The images obtained from oral inoculation studies indicate that the luminescent signal, at 2 days p.i. and at 7 days p.i., localizes almost entirely to the cecum in each of the animals (Popesko, et al., 1990, *A Colour Atlas of Anatomy of Small Laboratory Animals Vol. Two: Rat Mouse Hamster* (London England: Wolfe)) except those infected with LB5000lux. Luminescence is also apparent in the colon in some animals. By 7 days p.i., no luminescence is detectable in the LB5000lux-infected animals. The CFU present in the organs of these mice are determined at 2 and 5 d p.i.

In animals infected intragastrically with the invasive strain, SL1344lux, the luminescence in the cecum appears early and precedes a systemic infection. In contrast, infections with the non-invasive BJ66lux strain result in a persistent luminescence from the cecum that remains, in some animals, for the entire course of the study (8 days). By 8 days p.i., luminescence is detected over much of the abdominal surface, resembling the distribution of photons following an i.p. inoculation, in the SL1344lux infected mice.

Infections with SL1344lux appear to become systemic, as predicted, with progressively more photons being emitted from an increasing surface area. Luminescence appears to localize over the abdomen in infections with all strains with little detectable luminescence from outside this area. A large number of transmitted photons are localized as a single focus over the abdomen suggesting that even though the infection may be systemic, the greatest amount of replication may be in areas surrounding the intestine.

Localization of the luminescence over the cecum indicates that not only are there large numbers of organisms in this region of the intestine, but also suggests that the *Salmonella* associate with cells of the mucosa such that they can obtain sufficient oxygen for luminescence. Emission of photons from luciferase is oxygen dependent and the expected oxygen levels in the lumen of the cecum, or intestine in general, are below the levels required for luminescence. The luciferase reaction is not expected to be functional in the intestine unless the bacteria can obtain oxygen from cells of the intestinal epithelium.

Thus, the systemic infection seems to be related to the invasive phenotype and not to simply adherence to epithelial cells of the intestine. These experiments implicate the cecum in some role in the pathogenic process either in the carrier state or as a site of dissemination.

Monitoring the progression of infections to different tissues may greatly enhance the ability to understand these steps in the pathogenic process, and enable, the screening for compounds effective to inhibit the pathogen at selected steps.

Internal Imaging Following I.P. Inoculation. Mice infected intraperitoneally with SL1344lux are imaged before and after laparotomy (Example 9). The results are shown in FIG. 10. The images demonstrate luminescence over a majority of the abdomen with multiple foci of transmitted photons. The cecum does not appear to contain luminescent *Salmonella*. The results from these experiments indicate that all strains of *Salmonella* have sufficient $O_2$ to be luminescent in the early phases of infection. However, entry of *Salmonella* into cells of the mucosa and subsequent systemic infection is likely limited to strains with the invasive phenotype, since systemic infections at later time points are only apparent in SL1344lux-infected mice.

Effects Of Ciprofloxacin On *Salmonella* Infection. Experiments, detailed in Example 10, are performed to demonstrate that non-invasive imaging is useful for following the response of an infection to drugs. Mice are orally inoculated with SL1344lux and treated with 100 mg of ciprofloxacin, an antibiotic effective against *Salmonella* infections. The mice are imaged at selected time periods following treatment, and the extent of infection is quantitated by measuring photon emission. Photon emission in treated mice is compared to values before the initiation of treatment, and to values from control mice that had been infected, but not treated. Results from one such experiment are shown in FIGS. 11A, 11B, 11C, 11D, and 11E and discussed in Example 10. Infection is significantly reduced in mice treated with the antibiotic, compared both to the levels of pathogen at time zero in treated animals, and to levels of pathogen in control animals throughout the treatment period.

Effects Of Carbenenicillin Selection. Ducluzeau, et al., 1970, *Zeut. Bakt.* 5313:533–548., demonstrated that treatment of animals with antibiotics facilitated colonization of the cecum with *Salmonella* . The mice in the present experiments are maintained on an antibiotic regime of intramuscular injections of carbenicillin for the purpose of selecting the Amp$^r$ *Salmonella* containing the luciferase clone. This treatment may alter the course of the gastrointestinal infection, but the observation that *Salmonella* can associate with the cells lining the cecum indicates that oxygen is available for luminescence. This observation is notable, since the lumen of the cecum is commonly thought to be an anaerobic environment.

H. Applications

The bioluminescence technology is broadly applicable to a variety of hostpathogen systems and may also enable temporal and spatial evaluation of other biological events, as for example tumor progression and gene expression in living mammals, and have application in pharmaceutical development and screening. Widespread use of in vivo imaging of pathogens may reduce the numbers of animals and time needed for experiments pertaining to pathogenesis and/or the real-time study antimicrobial agents. Furthermore, bioluminescent organisms may be useful as biosensors in the living animal, much as luminescent bacteria are used in environmental analyses. Korpela et al., for example, demonstrate that the limited oxygen supply in the lumen of the G.I. tract restricted bioluminescence to sites in which oxygen is accessible to the *Salmonella* , perhaps directly from epithelial or other cell types. Korpela, et al., 1989, *J. Biolum. Chemilum.* 4:551–554. This oxygen requirement may find utility as an indicator of intimate cell-cell interactions, or as a biosensor for studying oxygen concentrations at various sites in living animals. In the following, several exemplary applications of this technology are described for the purpose of illustration, but are in no way intended to limit the present invention.

1. Determination of Oxygen Levels

The oxygen requirement for luminescence of luciferase evidenced in the experiments summarized above indicates that the present invention may be applicable as a method of determining spatial gradients of oxygen concentration in a subject. Luminescent bacteria have been used to measure oxygen levels in the range of 10–1 mM. The studies predict that 0.1 nM is the lower limit of detection (Campbell, 1988, *Chemiluminescence. Principles and Applications in Biology and Medicine* (Chichester, England: Ellis Horwood Ltd. and VCH Verlagsgesellschaft mbH)). The imaging methods described herein may be used for studying oxygen levels at various sites in living animals. For example, microorganisms that have been engineered to emit light in an $O_2$ or $Ca^{2+}$-dependent manner could be used as biosensors in a subject, much like luminescent bacteria are used in environmental analyses (Guzzo, et al., 1992, *Tox. Lett.* 64/65:687–693, Korpela, et al., 1989, *J. Biolum. Chemilum.* 4:551–554, Jassim, et al., 1990, *J. Biolum. Chemilum.* 5:115–122). The dynamic range of luminescence with respect to $O_2$ concentration is much broader and reaches lower $O_2$ concentrations than $O_2$ probes (Campbell, 1988, *Chemiluminescence. Principles and Applications in Biology and Medicine* (Chichester, England: Ellis Horwood Ltd. and VCH Verlagsgesellschaft mbH)). Moreover, light emission in proportion to $O_2$ concentration is linear over a range of 30 nM to 8 mM, and 9 mM $O_2$ is required for ½ maximal luminescence.

2. Localization of Tumor Cells

The growth and metastatic spread of tumors in a subject may be monitored using methods and compositions of the present invention. In particular, in cases where an individual is diagnosed with a primary tumor, LECs directed against the cells of the tumor can be used to both define the boundaries of the tumor, and to determine whether cells from the primary tumor mass have migrated and colonized distal sites.

For example, LECs, such as liposomes containing antibodies directed against tumor antigens and loaded with LGMs, can be administered to a subject, allowed to bind to tumor cells in the subject, imaged, and the areas of photon emission can be correlated with areas of tumor cells.

In a related aspect, images utilizing tumor-localizing LECs, such as those described above, may be generated at selected time intervals to monitor tumor growth, progression and metastasis in a subject over time. Such monitoring may be useful to record results of anti-tumor therapy, or as part of a screen of putative therapeutic compounds useful in inhibiting tumor growth or metastasis.

Alternatively, tumor cells can be transformed, transduced, transiently or permanently, or otherwise made to emit light, with a luciferase construct under the control of a constitutively-active promoter, and used to induce luminescent tumors in animal models, as described above. Such animal models can be used for evaluating the effects of putative anti-tumor compounds.

3. Localization of Inflammation

In an analogous manner to that described above, compositions and methods of the present invention may be used to localize sites of inflammation, monitor inflammation over time, and/or screen for effective anti-inflammatory compounds. Molecules useful for targeting to sites of inflammation include the ELAN family of proteins, which bind to selections. An ELAN molecule can be incorporated as a targeting moiety on an entity of the present invention, and used to target inflammation sites.

Alternatively, an animal model for the study of putative anti-inflammatory substances can be made by making the animal transgenic for luciferase under the control of the E-selectin promoter. Since E-selectin is expressed at sites of inflammation, transgenic cells at sites of inflammation would express luciferase.

The system can be used to screen for anti-inflammatory substances. Inflammatory stimuli can be administered to control and experimental animals, and the effects of putative anti-inflammatory compounds evaluated by their effects on induced luminescence in treated animals relative to control animals.

4. Localization of Infection

As illustrated in experiments performed in support of the present invention and summarized above, LGCs may be effectively used to follow the course of infection of a subject by a pathogen, including, but not limited to, *Pseudomonas, Staphylococcus, Streptococcus, Enterococcus, Enterobacter, Citrobacter, Leginella, Helicobacter, Acinetobacter, Escherichia, Klebsiella* or *Serratia*. In experiments detailed herein, the LGCs are pathogenic cells (*Salmonella*) transformed to express luciferase. Such a system is ideally-suited to the study of infection, and the subsequent spread of infection, in animal models of human diseases. It provides the ability to monitor the progression of an infectious disease using sites of infection and disease progression rather than traditional systemic symptoms, such as fever, swelling, etc. in studies of pathogenesis.

Use of an external imaging method to monitor the efficacy of anti-infectives permits temporal and spatial evaluations in individual living animals, thereby reducing the number of animals needed for experiments pertaining to pathogenesis and/or the study anti-infective agents.

5. Monitoring Promoter Activity in Transgenic Mice

The generation of transgenic animals has become an important tool in basic research and in the development of gene therapies and gene vaccines. The present invention provides methods for rapid in situ assessment of the uptake of nucleic acids and their expression and thus the evaluation of gene delivery systems and DNA-based therapies.

More specifically, luciferase expression may serve as a real-time bioluminescent reporter, allowing the noninvasive assessment of the level of promoter activity in living animals. Photons from the in vivo luciferase reaction in the transgenic animal are detected by a CCD camera, after transmission through animal tissues, and used as an indication of the level and location of gene expression. This way, a real-time assessment of the extent of promoter activity in both superficial and deep tissues can be accomplished.

As described in specific embodiments of the present invention, the light-emitting reporter systems in transgenic animals facilitate in vivo assessment of the regulation of gene expression, thus facilitating the development of novel therapies that target regulation of viral and host gene expression. Bioluminescent reporters offer the advantages of spontaneous emission of light without a need for outside light sources, low background signal permitting near single-event detection, real-time analyses, and the absence of cytotoxic photosensitizing dyes. As such, bioluminescent reporters have a greater versatility than fluorescent markers in mammalian tissues. Biological processes can be viewed in vivo by illuminating the temporal and spatial distribution of gene expression in animals and humans.

The in vivo monitoring of promoter activity as described herein can be used for the assessment of gene delivery and expression in gene therapies, gene vaccines, antisense oligonucleotide therapies, the generation of chimeric and transgenic animals in research. The technology is further useful for real-time noninvasive assays for gene expression in research environments involving questions of developmental regulation, response to infectious disease or other systems where gene expression demonstrates change.

The following examples are given to enable those skilled in the art to more clearly understand and to practice the present invention. The present invention is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. The present invention is explained in more detail by means of the below examples.

VI. EXAMPLES

A. Materials and Methods

1. Cells

*Salmonella* strains SL1344 and LB5000 were obtained from B. A. D. Stocker (Stanford University; Hoiseth and Stocker, 1981, *Nature* 291:238–239). *Salmonella* strain BJ66 was obtained from B. D. Jones (Stanford University).

HEp-2 cells were obtained from the American Type Culture Collection (ATCC; 12301 Parklawn Dr., Rockville Md.; Accession number CCL-23).

Murine peritoneal macrophages were obtained by peritoneal lavage of euthanized Balb/c mice with 7 ml of growth medium (Maximow and Bloom, 1931, *Textbook of Histology*, Saunders, Philadelphia.)

2. Static Cultures

Low oxygen (static) cultures were prepared by inoculating 3 ml of LB Broth containing 100 mg/ml of carbenicillin with 6 μl of a bacterial suspension from a stationary phase culture, and growing the bacteria at 37° C. overnight in a stationary 7 ml culture tube.

3. Mice

Balb/c (Ity$^{s/s}$) mice were obtained from the Department of Oncology, Stanford University. 129×Balb/c (Ity$^{r/s}$) mice were obtained from the Stanford Transgenic Animal Facility (Stanford, Calif.). All animals were housed under identical conditions of photo period, feeding regime and temperature in the Stanford University Research Animal Facility (Stanford, Calif.).

Anesthesia was performed by injecting the animals intraperitoneally (i.p.) with 33 μg/kg body weight nembutal.

Euthanasia was performed by asphyxiation in $CO_2$ or cervical dislocation, following protocols recommended by the Stanford University Research Animal Facility. Cervical dislocation was used in experiments in which results may have been affected by physiological changes due to asphyxia.

Mice infected with lux-transformed *Salmonella* were given daily intramuscular (i.m.) injections of carbenicillin (125 mg per kg body weight) to maintain selective pressure on the luminescent *Salmonella* for retention of the Amp$^r$ plasmid containing the lux operon.

4. Imaging

Animals or objects to be imaged were immobilized in a light-tight box containing a door and a charge-coupled device (CCD) camera with a two stage microchannel intensifier head (model C2400-40, Hamamatsu). The camera was attached, via cables leading out of the box, to an "ARGUS 50" image processor (Hamamatsu).

The ICCD system described above is capable of detecting single photons once a threshold of 10–30 photons is achieved. The signal to noise ratio of the system ranged from 2:1 to $1 \times 10^4$:1, depending on signal intensity.

Grey-scale images were obtained by opening the light box door in dim room light and integrating for 8–64 frames. The gain for the gray scale images was set to optimize the image—typically at 3000 volts on a scale of 0 to 10,000 volts.

Bioluminescence data were obtained in absence of external illumination. Exposure settings were as follows: the black level was set automatically by the camera/image processor, the gain was adjusted automatically by the intensifier controller, and the f-stop was set at 2.8. A 60 mm "AF NIKKOR" macro lens was used (Nikon Inc., Melville, N.Y.).

Bioluminescence images were generated by integrating photons for a selected period of time, typically 5 minutes. Data are presented at the lowest bit range setting of 0–3 bits per pixel for all animals. For images of other objects, i.e., 24 well plates, where the resolution of the bioluminescent signals was not possible at a bit range of 0–3, the range was increased to a setting that permitted localization of bioluminescent signals, typically 1–7. Objects were imaged for shorter periods of time when additional information could not be obtained by imaging for five minutes.

External imaging refers to non-invasive imaging of animals. Internal imaging refers to imaging after a partial dissection of the animals, typically a laparotomy. Internal imaging is performed in selected animals to confirm the sources of photon emission localized by external imaging.

The bioluminescence image data are presented as a pseudo-color luminescence image representing the intensity of the detected photons. Six levels of intensity are typically used, ranging from blue (low intensity) to red (higher intensity).

To generate the FIGURES presented herein, greyscale and bioluminescence images were superimposed, using the image processor, to form a composite image providing a spatial frame of reference.

The composite image was displayed on an RGB CRT (red, green, blue; cathode ray tube) monitor, and the monitor was photographed to produce hardcopies. Hardcopies were also generated by saving the image processor image as a digital file, transferring the file to a computer, and printing it on a color printer attached to the computer. Alternatively, hardcopies may be generated by printing the video signal directly using a video printer.

B. Example 1

Transformation of *Salmonella* with pCGLS1 lux Plasmid

*Salmonella* strains SL1344, BJ66 and LB5000 were transformed with pCGLS1, a pUC18-based vector encoding the lux operon from *Xenorhabdus luminescens* (Frackman, et al., 1990).

1. pCGLS1 Plasmid

Figure 1C:
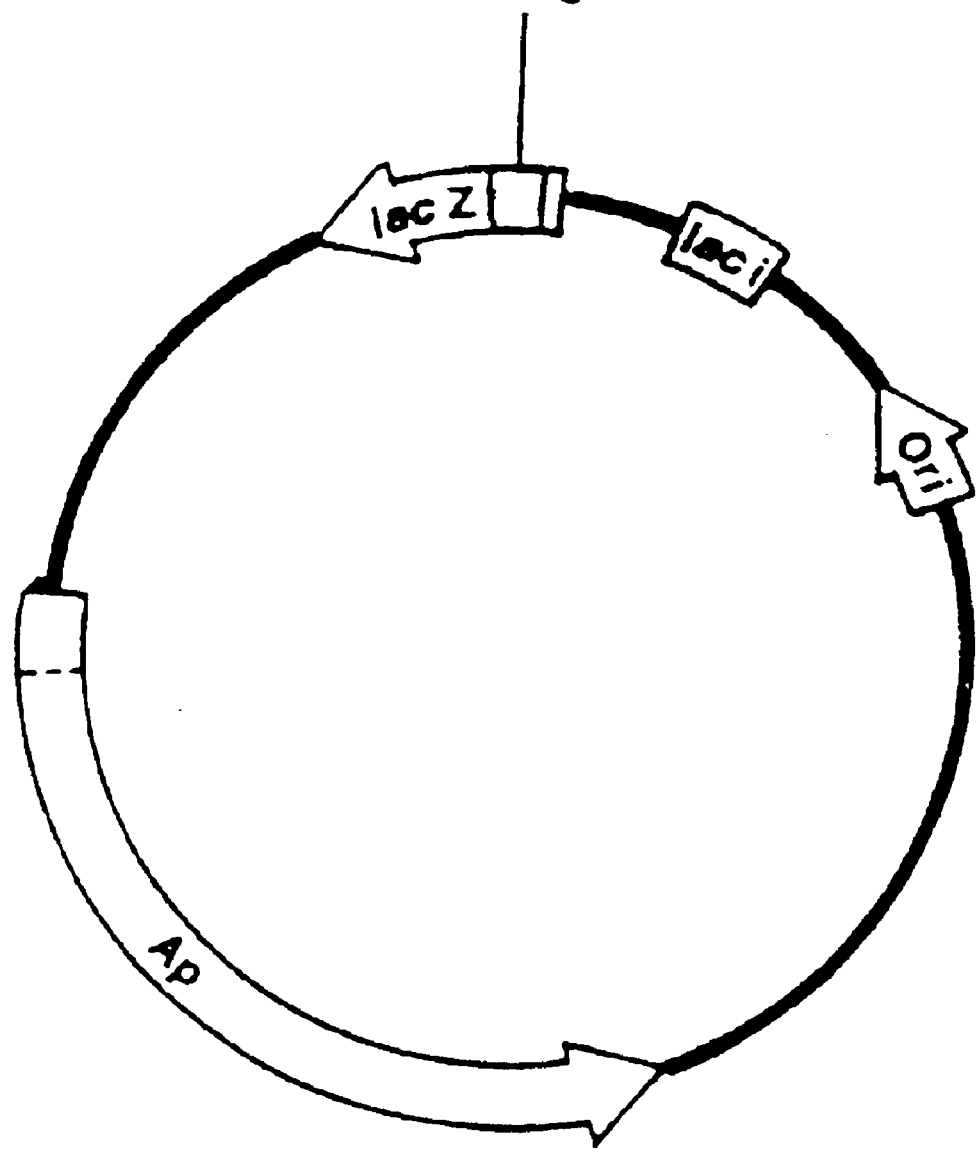

A schematic of the pCGLS1 plasmid is shown in FIGS. 1A, 1B and 1C. The plasmid was constructed by cloning an ~11 kb region encoding the lux genes from the soil bacterium *Xenorhabdus luminescens* (FIG. 1A; Frackman, et al., 1990) into the Bam HI site (FIG. 1B) of pUC18 (FIG. 1C; Clontech, Palo Alto, Calif.). The construction of the vector is described by Frackman, et al., (1990).

Restriction enzyme sites in FIG. 1A are represented as follows: Bs, Bst EII; C, Cla I; E, Eco RI; H, Hind III; M, Mlu I; S, Sca I; X, Xba I; B/Sa, Bam HI and Sau 3A junction. A sequence included in the multiple cloning site (MCS) is provided in FIG. 1B, with the Bam HI site indicated in bold type.

A graphical representation of a pUC18 vector with no insert is shown in FIG. 1C. Labeled elements include an ampicillin resistance gene (Ap), a lac Z gene (lac Z) and an *E. coli* origin of replication (Ori). The unmodified pUC18 vector is approximately 2.7 kb in size.

2. Transformation of *Salmonella*

Electrocompetent cells from *Salmonella* strains SL1344, BJ66 and LB5000 were made using standard methods (Sambrook, et al., 1989, In *Molecular Cloning: A Laboratory Manual*, Cold Spring Harbor Laboratory Press, Vol. 2) and stored at −80° C. until just prior to use. Electroporation was performed as follows: 1 μl of the plasmid (0.2 μg/ml) was added to 40 μl of ice-cold electrocompetent cells suspended in 10% glycerol. The suspension was mixed gently for one minute, placed in a 1 mm gap electroporation cuvette and electroporated using a Bio-Rad Gene-Pulser (Bio-Rad Laboratories, Hercules, Calif.). The settings were 2.5 kvolts, 400 ohms and 25 μfarads.

Following a one hour agitated incubation in Luria Bertini (LB) broth at 37° C., the cells were plated on (LB) Agar containing 100 μg/ml carbenicillin and allowed to grow overnight.

To maximize the bioluminescence of the labelled *Salmonella*, the lux operon was maintained on a high-copy-number plasmid and not integrated as a single copy gene. However, plasmids are subject to modification by the bacterial cell especially in recA strains, such as SL1344 and BJ66 used in this study. The recA locus encodes a recombinase that may delete regions of the plasmid containing the lux operon and the β-lactamase. Therefore, *Salmonella* recovered from cells in culture were plated both in the presence or absence of carbenicillin, and were imaged to determine the frequency at which bioluminescence was lost. All colonies recovered from gentamicin-treated, lysed HEp-2 cells and macrophages were ampicillin resistant (Amp$^r$) and bioluminescent. Therefore, lux genes appeared not to be lost during co-culture with mammalian cells.

Colonies were assayed for luminescence by visual inspection in a dark room. Five transformants were identified as having high levels of luminescence. Three of these, one each from the SL1344, BJ66 and LB5000 strains, were selected for subsequent experiments. They were termed SL1344lux, BJ66lux and LB5000lux, respectively.

C. Example 2

Invasive Potential of Normal and Transformed *Salmonella*

The invasive potential of six strains of *Salmonella* (SL1344lux, LB5000lux, BJ66lux, SL1344, LB5000 and BJ66) was determined using two types of bacterial adherence and entry assays. Colony-forming units (CFU) assays were performed essentially as previously described (Finlay and Falkow, 1989, *Mol. Microbiol.* 3:1833–1841) with modifications (Lee, et al., 1990, *PNAS* 87:4304–4308). Bioluminescence assays were performed essentially like the CFU assays, except that the number of cells was quantitated using bioluminescence, as opposed to CFUs.

Briefly, HEp-2 cells and primary murine peritoneal macrophages were seeded into 24-well tissue culture dishes at $1 \times 10^5$ cells per well in RPMI (Gibco/BRL, Grand Island, N.Y.) supplemented with 20 mM glutamine (Gibco/BRL) and 5% fetal calf serum (Hyclone, Logan, Utah). Twenty four hours (HEp-2) or seven days (macrophages) after cell seeding, bacteria from static cultures (see "Materials and Methods", above) were inoculated at $1 \times 10^6$ (multiplicity of infection (m.o.i.) of 10) or $1 \times 10^7$ (m.o.i. of 100, columns on right in FIGS. 2B, 2C, 2D, and 2E) organisms per well and centrifuged onto the cell monolayer for 5 minutes at 1000 rpm (185×g) in a Beckman clinical centrifuge (Beckman Instruments, Columbia, Md.). The medium was replaced with RPMI medium (Gibco/BRL) either with (entry assay)

or without (adherence assay) gentamicin (100 mg/ml). The co-cultures were incubated for a total of 3.5 hours at 35° C. in 5% $CO_2$.

Gentamicin in the incubation medium kills bacteria that had not been internalized by the HEp-2 cells, including those adhering to the surfaces of the HEp-2 cells. Accordingly, the signal in adherence assays (without gentamicin) represent both adherent and internalized bacteria, whereas the signal in entry assays (with gentamicin) represent only internalized bacteria.

Adherence and entry were assayed by imaging luminescent bacterial cells at three timepoints—1.5, 3.0 and 3.5 hours post inoculation. Prior to imaging at the first timepoint, the cell monolayer was washed three times with phosphate-buffered saline (PBS) to remove unattached bacteria and a fresh aliquot of RPMI medium was added. Luminescence was recorded using a 30 second exposure. Images at the second and third timepoints were obtained using a similar exposure, but without first washing the cells.

Data recorded at the last timepoint, displayed as pseudo-color luminescence images superimposed over gray scale images of the culture dish wells, are shown in FIG. 2A. The cell types, *Salmonella* strains, and usage of gentamicin are indicated in the FIGURE. The data are also summarized as relative intensity of photon counts in the graphs in FIGS. 2B and 2D.

Following imaging at the 3.5 hour timepoint, the tissue culture cells were washed three times with PBS and lysed with 0.2% "TRITON X-100" in PBS. Adherent and/or intracellular bacteria, released by lysis, were plated on LB- or LB-carbenicillin agar plates and incubated for 18 h at 35° C. The number of bacteria released from each well was determined by counting the number of colony forming units (CFU, Finlay and Falkow, 1989, *Mol. Microbiol.* 3:1833–1841. Lee, et al., 1990, *PNAS* 87:4304–4308). These data are represented as the total bacterial colonies per ml recovered from co-culture after incubation for 3.5 h with or without gentamicin, and are summarized in the graphs in FIGS. 2C and 2E.

Data from both the bioluminescence and CFU assays indicate that (i) *Salmonella* transformed with the lux genes have an infective potential similar to that of the parent lines, and (ii) luminescence detection and CFU determination yield comparable estimates for the invasive potential of the two *Salmonella* strains in HEp-2 cells and macrophages. The ratio of bioluminescence to CFU was lower in macrophage cultures, possibly due to the subcellular compartment in which the *Salmonella* enter macrophages.

D. Example 3

In vitro Luminescence of Transformed *Salmonella*

10 μl of four 10-fold serial dilutions (ranging from $10^6$ cells to $10^3$ cells per ml) of LB5000lux *Salmonella* were placed in four 100 μl glass capillary tubes (Clay-Adams div. of Becton Dickinson, Parsippany, N.J.). The bacterial suspensions formed columns of fluid in the tubes, with pockets of air at both ends. One end of each tube was sealed with critoseal (Clay-Adams). The medium in which dilutions were made was saturated with $O_2$ through exposure to air.

The tubes were wrapped with clear plastic wrap and luminescence was determined by imaging for 30 seconds as described above. An exemplary image is shown in FIG. 3A. Four tubes are pictured. They contained (from top to bottom) $10^6$, $10^5$, $10^4$ and $10^3$ *Salmonella* cells/ml ($10^4$, $10^3$, $10^2$ and 10 cells/tube). Luminescence could be detected in suspensions containing as few as $10^4$ cells/ml (100 cells). The luminescence is confined, however, to air/liquid interfaces, suggesting that the luminescence reaction requires relatively high levels of oxygen. Since many of the cells are presumably in the fluid column and not at the air/fluid interfaces, the data suggest that the luminescence in the capillary tubes shown in FIG. 3A arises from considerably fewer than the total number of cells in each tube.

E. Example 4

In vitro Detection of Luminescence through Animal Tissue

Micro test-tubes, constructed from glass capillary tubing with an internal diameter of 3.5 mm, containing serial dilutions of LB5000lux *Salmonella* were prepared essentially as described in Example 3, above. In the present example, however, the bacterial suspensions contacted the sealed end of the tube and were exposed to air only at the upper end. The tubes were placed in a translucent plastic scintillation vial and surrounded by one of the following animal tissues: chicken breast muscle, chicken skin, lamb kidney or lamb renal medulla. All tissues were obtained from the meat department of a local supermarket (Safeway, Mountain View, Calif.).

A diagram of a vial containing a capillary tube surrounded by tissue is shown in FIG. 5. The vial 1 is approximately 1.4 cm in diameter and includes a cap 2. The vial is coated with an opaque material (i.e., black tape) along its upper portion 3. Animal tissue 4 is placed in the vial such that it extends from the bottom of the vial to just above the bottom edge of the opaque coating 3. The micro test-tube 5 is sealed at the bottom by a plug 7 (i.e., a crytoseal plug), and is centered radially in the vial, with the plugged end of the tube touching or in close proximity to the bottom of the vial. The bacterial suspension 6 extends approximately 1 cm upward from the bottom of the tube.

Photons emitted from vials with and without tissue, and with and without bacteria, were counted using a liquid scintillation counter (model 1219 Rackbeta, LKB/Wallac, Gaithersburg, Md.) with the fast coincidence discriminator disabled.

Controls without tissue were assayed by placing the bacterial suspension directly in the scintillation vial. All experiments were performed in triplicate.

In each experiment, the vials were counted two to three times, rotating the vial 90° between each count, to control for effects of possible tissue thickness inconsistency. No significant differences were detected.

The results are summarized in TABLE I, below.

TABLE I

TRANSMISSION OF PHOTONS THROUGH TISSUE

| Sample | Chicken skin | Chicken muscle | Lamb kidney | Lamb medulla |
|---|---|---|---|---|
| Vial alone | $2.1 \times 10^4$ | $1.3 \times 10^4$ | $1.0 \times 10^4$ | $1.0 \times 10^4$ |
| Tissue alone | N.D. | $1.5 \times 10^4$ | $9.4 \times 10^3$ | $8.5 \times 10^3$ |
| Tissue and LB5000lux* | $2.7 \times 10^5$ | $2.3 \times 10^5$ | $1.6 \times 10^4$ | $1.5 \times 10^5$ |
| LB5000lux* alone | $2.0 \times 10^6$ | $1.7 \times 10^6$ | $4.8 \times 10^6$ | $4.8 \times 10^6$ |

Counts are averages of triplicate measurements, tissue path length was 1 cm.
*$1 \times 10^7$ cells.

The signal for 1×10³ LB5000lux in kidney tissue was at or near background levels using, the photomultiplier tubes (PMT) in the scintillation counter. The background in this type of detection is due to the dark current of the PMT and limits the studies to analysis of rather intense signals.

Bioluminescence from approximately 1×10⁷ LB5000lux was detectable through 0.5 cm of avian muscle, skin ovine renal medulla and ovine kidney. These results indicate that bioluminescence from the labeled *Salmonella* was detectable through animal tissues of variable opacity. Since oxygen was likely limited in the capillary tubes (as demonstrated in FIG. 3A), it is likely that fewer numbers of bioluminescent *Salmonella* could be detected through tissue than are indicated in this assay.

F. Example 5

In vivo Detection of Bioluminescent *Salmonella*

To assess the availability of oxygen to *Salmonella* during infection, wild-type SL1344lux was inoculated into the peritoneal cavity (i.p.) of BALB/c mice. Photons emitted from the bacteria internally, and transmitted through the abdominal wall were externally detected and localized in anaesthetized mice using an intensified CCD camera 24 h after inoculation (FIG. 3B). Systematic *Salmonella* infections are thought to involve colonization of the lymph nodes, spleen, liver for Ventral images of the mice infected by i.p. inoculation of wild-type SL 1344lux demonstrated transmitted photons over much of the abdominal surface, with foci of various intensities (FIG. 3B). These results were consistent with widespread colonization of the viscera, possibly including the liver and mesenteric lymph nodes, and indicate that the level of available oxygen in some tissues can be adequate for external detection of bioluminescence from the labelled pathogen.

G. Example 6

Effect of Human Blood on the Light Emission from Bioluminescent *Salmonella*

As demonstrated in the following example, fewer than ten (10) bacterial cells can be detected with an intensified CCD detector.

Two fold serial dilutions of *Salmonella*, strain LB5000, that had been transformed with a plasmid that conferred constitutive expression of the luciferase operon were plated in duplicate into 96 well plates. Dilutions were made in 30 µl of growth medium alone (indicated as LB5000) and with 30 µl of blood to determine the effects of blood as a scattering and absorbing medium on the limits of detection. Each dilution and the numbers of colony forming units (CFU) implied from plating samples from concentrated wells are indicated in FIG. 4. The relative bioluminescence for each well as determined by analysis of the image generated by the CCD detector is shown (Table III). The signal in the more concentrated wells was off scale and the numbers are therefore not linear at higher concentrations.

TABLE III

| Dilution | Relative Bioluminescence | |
|---|---|---|
| | LB5000 | LB5000 and 30 µl blood |
| 1:100 | 199243 | 159497 |
| 1:200 | 187163 | 110081 |
| 1:400 | 170044 | 72234 |
| 1:800 | 154031 | 46273 |
| 1:1600 | 146934 | 17598 |
| 1:3200 | 112196 | 6731 |
| 1:6400 | 50302 | 320 |

H. Example 7

Detection of Orally-Administered lux *Salmonella* in Balb/c Mice

Balb/c mice were infected by oral feeding (Stocker, et al.) with a 50 µl suspension of 1×10⁷ virulent SL1344lux, non-invasive BJ66lux and low virulence LB5000lux *Salmonella*. The mice, 4–6 weeks of age at the time of infection, were imaged daily with 5 minute integration times (photon emission was measured for 5 minutes). Prior to imaging, the mice were anesthetized with 33 µg/kg body weight nembutal.

Representative images are shown in FIGS. 6A, 6B, and 6C. At 24 hours post inoculation (p.i.), the bioluminescent signal localized to a single focus in all infected animals (FIGS. 6A, 6B, and 6C). Bioluminescence disappeared in all animals infected with the low virulence LB5000lux by 7 days p.i. (FIG. 6A). In BALB/c mice infected with the wild-type SL1344lux, bioluminescence was detected throughout the study period, with multiple foci of transmitted photons at 8 d. In these animals, the infection frequently spread over much of the abdominal cavity (FIG. 6C). In one-third of these animals, transmitted photons were apparent over much of the abdominal area at 8 d, resembling the distribution of photons following an i.p. inoculation (see FIGS. 3B and 6F). The spread of infection by BJ66lux was more variable, but the infection typically persisted and remained localized at the initial site (FIG. 6B).

After infection of resistant BALB/c×129 mice with wild-type SL 1344lux, the bioluminescent signal remained localized and persistent in a group of 10 mice throughout the study period. This result was in contrast to the disseminated bioluminescence observed in SL1344lux-infected susceptible mice (Ity$^{r/s}$) (see, Example 9 and FIGS. 8A and 8B), but resembled the persistent infection of susceptible BALB/c mice with the less invasive BJ66lux. As a control, *Salmonella* were cultured from persistently infected resistant BALB/c×129 mice, and 80–90% of the colonies recovered after 8 d were Amp$^r$. Of these, more than 90% were bioluminescent, suggesting that observed differences were not due to significant loss of lux plasmid, but rather were due to real differences in pathogenicity of the bacterial strains.

I. Example 8

Detection of Infection Following I.P. Inoculation with a Virulent and a Low Virulence Strain of *Salmonella*

Balb/c mice were infected with either virulent (SL1344lux) or low virulence (LB5000lux) *Salmonella* by intraperitoneal (i.p.) inoculations of 1×10⁷ bacterial cells in a 100 µl suspension, without simultaneous injection of air.

At 32 hours post injection (p.i.), the mice were anesthetized and imaged as described above. The results are shown in FIG. 7. Widespread infection is evident in the two mice in the left part of FIG. 7, infected with the virulent SL1344lux strain. In contrast, little, if any, luminescence is detected in the mice on the right, injected with the low virulence LB5000lux strain.

J. Example 9

Detection of Systemic Infection in Resistant Mice Following Oral Inoculation with *Salmonella*

Resistant 129×Balb/c (Ity$^{r/s}$) viable mice were infected by intragastric inoculation of 1×10⁷ SL1344lux *Salmonella*. The bacteria were introduced through an intra-gastric feeding tube while under anesthesia. The animals were imaged daily for 8 days post injection (d.p.i.).

Results are shown in FIGS. 8A and 8B. Mice, in triplicate, were infected and imaged daily for 8 days. Exemplary images for day 1 (FIG. 8A) and day 8 (FIG. 8B) are shown. These data indicate that mice resistant to systemic *Salmonella* infection have a localized chronic infection in the cecum, but that the infection does not spread into the abdominal cavity.

K. Example 10

Post-Laparotomy Imaging Following Oral Inoculation with *Salmonella*

Laparotomy was performed following oral inoculation of *Salmonella* to precisely localize the luminescent signal within the abdominal cavity, and to compare this localization with that obtained using non-invasive imaging. The animals were inoculated as described in Example 9. After a selected period of time, typically seven days, the mice were anesthetized and externally-imaged, as described above. An exemplary image is shown in FIG. 9A. After external imaging, the peritoneal cavity was opened and the animals were imaged again, as illustrated in FIG. 9B. In some instances the mice were imaged a third time, following injection of air into the lumen of the intestine both anterior and posterior to the cecum (C) (FIG. 9C). The mice were euthanized immediately after the final imaging.

In each case where a focal pattern of bioluminescence was observed in susceptible mice, early in infection after oral inoculation, photons originated almost exclusively from the cecum, while variations in the precise localization and intensity of focal bioluminescence were due to variable positioning of the cecum. The focal pattern of bioluminescence observed in infection-resistant BALB/c×129 mice similarly localized to the cecum. In contrast, such localization was not observed in animals infected i.p. with SL1344lux (FIG. 3B). At late stages in infection-susceptible mice inoculated orally with the wild-type SL1344lux, bioluminescence was multifocal, however, additional foci of luminescence did not become apparent after laparotomy. In mice infected with the less-virulent LB5000lux, bioluminescence was not detectable at 7 d in any tissue or organ, even focally, after removal of the skin and peritoneal wall.

Bioluminnescence was not detected optically in the spleen or bloodstream of any infected animal; bioluminescence from the liver was seen only at later stages of disease; and bioluminescence from the G.I. tract was restricted to the cecum early in the disease course. This pattern could be due to differences in the numbers of *Salmonella* in the different tissues, or lack of available oxygen. The Amp$^r$ cfu present in homogenized organs of orally infected mice were quantified to evaluate the distribution of labelled *Salmonella* SL1344lux. Greater than 90% of the amp$^r$ bacterial colonies obtained from all analyzed tissues of SL1344lux-infected BALB/c mice at 7 d indicated total cfu from the liver, spleen, and lungs were in the range of $1.9 \times 10^3$ to $>1.0 \times 10^5$ without detectable photon emission, in vivo (TABLE II). In contrast, bioluminescence was detectable from the cecum and this tissue contained $>1.0 \times 10^8$ total cfu. No cfu were detectable in any tissue of the LB5000lux infected mice. These results suggest that $1 \times 10^6$ organisms in tissue is near the limit of detection at this emission wavelength using the current experimental system.

Oxygen is an essential substrate for the luciferase reaction, thus only *Salmonella* present in oxygenated microenvironments should be bioluminescent. The absence of bioluminescence from *Salmonella* in the anaerobic environment of the lumen of the G.I. tract is therefore predictable, and exposure of the intestinal lumen to air should reveal the presence of bacteria previously not detectable due to a lack of oxygen. In support of this view, one animal with detectable bioluminescence in the cecum alone excreted a faecal pellet that rapidly became bioluminescent upon exposure to air. This indication of non-luminescent, luciferase-expressing bacteria in the lumen of the intestine and the clear delineation of the aerobic and anaerobic zones in this tissue, suggested that injection of air into the lumen of the intestine would reveal the presence of additional bacteria. Injection of air into the lumen of the ileum and colon of another animal, with a similar pattern of bioluminescence, resulted in detectable photons near the injection sites (FIG. 9). Last, when a third mouse with cecal bioluminescence was killed, bioluminescence quickly ceased. Air was injected at other tissue sites because of the lack of clear zones of aerobic and anaerobic environments.

TABLE II

Colony-forming units in homogenized tissue from mice infected with bioluminescent Salmonella

| Strain | Tissue | Animal Number | Tissue Weight (mg) | Total cfu |
|---|---|---|---|---|
| SL1344lux | Liver | 1 | 441 | $1.9 \times 10^3$ |
|  |  | 2 | 778 | $2.5 \times 10^4$ |
|  | Spleen | 1 | 218 | $1.2 \times 10^4$ |
|  |  | 2 | 248 | $4.9 \times 10^5$ |
|  | Mesenteric lymph node | 1 | 76 | $>1.0 \times 10^6$ |
|  |  | 2 | 46 | $>1.0 \times 10^6$ |
|  | Lung | 1 | 17 | $1.5 \times 10^3$ |
|  |  | 2 | 69 | $2.7 \times 10^3$ |
|  | Cecum | 1 | 351 | $>1.0 \times 10^{8}$* |
|  |  | 2 | 422 | $>1.0 \times 10^{8}$* |

*Photons emitted from bacteria at these tissue sites were externally detected.

L. Example 11

Post-Laparotomy Imaging Following I.P. Inoculation with *Salmonella*

Balb/c mice were infected by intraperitoneal inoculation of $1 \times 10^7$ *Salmonella* (SL1344lux) as described in Example 8. Exemplary images of one such animal are shown in FIGS. 10A, 10B and 10C.

At 24 hours post-injection (p.i.), the animal was anesthetized and imaged for five minutes (FIG. 10A). The peritoneal cavity was opened and the mouse was imaged again for five minutes (FIG. 10B). The cecum was pulled to the left side, and the animal was again imaged for five minutes (FIG. 10A).

The results demonstrate that the localization of infection sites obtained with non-invasive imaging correlates well with the sites as revealed upon opening the peritoneal cavity.

M. Example 12

Effects of Ciprofloxacin Treatment on Bioluminescence from SL1344lux *Salmonella*

To demonstrate the utility of in vivo imaging, an infected animal was treated with the antibiotic ciprofloxacin, which known to be effective against systemic *Salmonella* infections. Magalianes, et al., 1993, *Antimicrobial Agents Chemo.* 37:2293.

Experimental and control groups of Balb/c mice were orally inoculated with SL1344lux. At 8 days p.i., mice in the experimental group were injected i.p. with 100 mg of ciprofloxacin hydrochloride (3 mg/kg body weight; Sigma Chemical Co., St. Louis, Mo.). Following treatment of the experimental group, animals from both groups were imaged (as above) at several intervals over a period of 5.5 h post treatment.

Representative images are shown in FIGS. 11B, 11C, 11D, and 11E. FIGS. 11B and 11D show composite images of representative animals from the control and treated groups, respectively, immediately before initiation of treatment of the experimental group. FIGS. 11C and 11E show composite images of the same animals 5.5 hours after initiation of treatment. Bioluminescence over the abdomen of the ciprofloxacin-treated animal was reduced to undetectable levels during this period of time, while bioluminescence in the control typically increased 7.5-fold. The total number of photons detected over the abdominal area were determined, normalized to the value at t=0, and plotted in FIG. 11A with respect to time post-treatment.

The data demonstrate that methods and compositions of the present invention can be used to evaluate the effects of drugs on the spread of infection in vivo.

N. Example 13

Bioluminescent Reporter for Promoter Activity in Cultured Cells

In order to demonstrate how the promoter from HIV (human immunodeficiency virus) responds to viral infection over time, jurket cells transfected with a plasmid containing the HIV LTR (long terminal repeat, promoter) upstream of the coding sequence of firefly luciferase were infected with a laboratory isolate of HIV-1 (strain A111) using standard laboratory conditions and followed for a period of 7 days (d) for emission of bioluminescent light. After 24 h, 60 h, 96 h, and 7 d, a gray scale image of the plate was generated in low room light followed by collection of photons emitted from the cultured cells in complete darkness for a period of 10 min. A color pseudoimage representing the intensity of bioluminescent light was superimposed over the gray scale image of the plate (FIG. 12). At 7 d post infection a clear signal is present in the duplicate cultures indicating high levels of replication (FIG. 12). The images at different time points represent the same two wells. Advantages of this assay for HIV replication are that: i) temporal studies can be done in a minimum number of wells since the same wells are followed over time, ii) kinetics of replication can therefore be studied as a phenotypic characteristic of viral isolates, iii) samples of cells or supernatant do not have to be collected, iv) the level of viral replication is almost immediately apparent, v) the detection could be set up remotely limiting human handling, vi) antiviral drugs could be evaluated in culture with the above listed advantages.

O. Example 14

Assessing Promoter Activity in Tissues of Transgenic Mice

Transgenic mice containing a construct composed of the regulatory portion of the HIV LTR (U3 region) upstream of the coding sequence of the firefly luciferase gene were generated and evaluated for the emission of photons after transmission through tissues. A diagram of the construct is shown at the bottom of FIG. 13. Numbers along the construct indicate nucleotide positions relative to the start of transcription. Sequences matching known motifs of cellular transcription factors are indicated with the names of the factors. Transcription from the HIV LTR was activated in the right ear of each two animals with a single topical application of dimethyl sulfoxide (DMSO). The animal on the left in FIG. 13 was given 150 μl of an aqueous solution of the substrate luciferin (50 mg/ml) via intraperitoneal (i.p.) injection. The animal on the right was not given substrate. 20 min. post treatment with substrate the animals were imaged as described for the plate in FIG. 12 with a 20 min. integration time. The color pseudoimage indicates light emission over the right ear (B) of the animal on the left, and not from the uninduced ear (A) or the animal that was not given substrate (C,D). This is the first demonstration of monitoring promoter activity in a living adult animal and demonstrates the relatively tight regulation of the LTR with DMSO induction. This technology allows for the temporal and spatial analyses of transcriptional activity in living animals.

P. Example 15

Topical Delivery of Substrate to Dermal Cells in Transgenic Animals

In order to optimize delivery of substrate, the substrate was topically delivered to dermal cells. The HIV LTR was induced in the skin of mice with twice daily treatments of DMSO over the entire surface of the back and the right ear for two consecutive days. Substrate was applied to the skin in solutions prepared in DMSO. Concentrations included 200 mM, 100 mM, 50 mM, 25 mM, and 12.5 mM. 5 μl of each concentration were spotted, in quadruplicate, on the backs using a multichannel pipette with the highest concentrations near the head. 5 μl of the 50 mm solution was applied to each ear. 2 min. after application the animal was imaged as described in FIG. 12. The bioluminescent response appeared increase linearly over the concentrations from 12.5 mM to 100 mM (FIG. 14). Bioluminescence from spots containing 200 mM luciferin was roughly equivalent to that from the 100 mM spots, solutions of luciferin containing water, in contrast, resulted in no detectable bioluminescence (FIG. 14). Solutions of 25% $H_2O$ in DMSO to 100% $H_2O$ were tested.

Q. Example 16

Induction of Bioluminescence in Ears of Transgenic Animals by Topical Luciferin Delivery The experiment of induction of luciferase expression in ears and systemic luciferin delivery of Example 14 was repeated with topical administration of substrate in 100% DMSO (FIG. 15). Signals from the ears were uniform and had greater intensity than with systemic luciferin delivery. See, FIGS. 13 and 15. Peak light emission was observed immediately after topical treatment compared to 20–30 min. after systemic administration of substrate.

R. Example 17

Unilateral Induction of Luciferase Expression in Transgenic Mice

The left half of the shaved dorsal surface of the transgenic animals and the left ear were treated twice daily for two days with DMSO to activate expression of the HIV-1 LTR. Luciferin was applied topically over the entire surface of the back and both ears, and animals were imaged immediately after addition of substrate. Unilateral emission of bioluminescence corresponding to the induced region was observed (FIG. 16).

S. Example 18

Bioluminescence Detectable in Internal Tissues of Transgenic Animals

Bioluminescence was detectable from the abdomens of animals treated with DMSO on one ear only. This signal is assumed to be due to ingestion of DMSO during grooming (FIG. 17).

T. Example 19

Localization of Internal Bioluminescence in Transgenic Mice

Animals demonstrating signal from the abdomen were laprotomized and imaged. Bioluminescent signal localized to the colon in 4 of 4 animals studied and in the animals shown in FIG. 18 was tightly localized to a region of the colon about 1 cm in length. In the other animals the entire colon appeared to emit bioluminescent light.

U. Example 20

Expression of the HIV-LTR in Neonatal Transgenic Mice

As the demonstrated in the following experiment, the HIV-LTR is differentially expressed through development.

4 d old transgenic mice were given intraperitoneal injections of luciferin in aqueous solution (15 $\mu$l at 50 mM), and imaged with integration times of 20 min. In the absence of any known inducing agent or treatment, bioluminescent signal indicative of expression of luciferase form the HIV LTR was apparent as a diffuse signal over much of the surface of the animal with more intense signal originating from the developing eye and extremities (FIG. 19). These data demonstrate that the LTR is inherently active in neonatal transgenic mice, and may be expressed to a greater level in the eyes and other locations.

All references are hereby incorporated in their entirety.

What is claimed is:

1. A non-invasive method for detecting expression of a heterologous gene in a living, non-human, mammalian subject, said method comprising
   providing a mammalian subject whose cells comprise a transgene, wherein (i) said transgene comprises a heterologous gene that encodes a fluorescent protein, (ii) expression of the heterologous gene is mediated by a promoter and (iii) said subject comprises opaque tissue; and
   measuring photon emission through opaque tissue of said subject wherein said photon emission is mediated by excitation of said fluorescent protein expressed from said heterologous gene.

2. The method of claim 1, wherein said measuring is done using a photodetector device.

3. The method of claim 2, wherein said measuring is carried out with an intensified charge-coupled photodetector device.

4. The method of claim 2, wherein said measuring is carried out with a cooled charge-coupled photodetector device.

5. The method of claim 1, wherein said measuring is carried out using fiber optic cables.

6. The method of claim 5, wherein said fiber optic cables terminate in a tightly-packed array.

7. The method of claim 5, wherein said fiber optic cables detect light from a limited defined region of the subject.

8. The method of claim 1, wherein said fluorescent protein is green fluorescent protein, lumazine, or yellow fluorescent protein.

9. The method of claim 1, wherein an input of light to excite the fluorescent protein is produced by a laser.

10. The method of claim 1, further comprising constructing a photon emission image from said measured photon emission.

11. The method of claim 10, further comprising
    acquiring a reflected light image of the subject, and
    superimposing said image of photon emission on said reflected light image to form a composite image.

12. The method of claim 1, wherein said expression of the heterologous gene is mediated by a constitutively active promoter.

13. The method of claim 1, wherein said expression of the heterologous gene is mediated by an inducible promoter.

14. The method of claim 13, wherein said inducible promoter is an interferon-inducible promoter.

15. The method of claim 13, wherein said inducible promoter is a promoter expressed in a disease state or a tissue-specific promoter.

16. The method of claim 15, wherein said disease state is inflammation.

17. The method of claim 16, wherein said promoter is E-selectin.

18. The method of claim 15, wherein said disease state is a tumor.

19. The method of claim 1, wherein expression of said heterologous gene is by a tumor cell.

20. The method of claim 1, further comprising:
    repeating said detecting at selected intervals,
    wherein said repeating is effective to track localization of the expression of the heterologous gene in the subject over time.

21. The method of claim 1, further comprising
    administering a compound to said subject, and
    measuring photon emission from said subject after administration of said compound.

22. The method of claim 21, further comprising:
    repeating at selected intervals said measuring after administration of said compound,
    wherein said repeating is effective to track an effect of said compound on a level of expression of said heterologous gene in said subject over time.

23. The method of claim 1, wherein said method fluiher comprises, prior to said detecting, placing the subject in a detection field of the photodetector device.

24. The method of claim 1, wherein photons that make up said photon emission are visible light photons.

25. The method of claim 1, wherein said measuring consists of measuring photon emission from within the subject with a photodetector device located outside of the subject.

26. The method of claim 25, wherein the measuring is done using a photodetector device.

27. The method of claim 26, wherein said measuring is canied out with an intensified charge-coupled photodetector device.

28. The method of claim 26, wherein said measuring is carried out with a cooled charge-coupled photodetector device.

29. The method of claim 25, wherein said measuring is carried out using fiber optic cables.

30. The method of claim 29, wherein said fiber optic cables terminate in a tightly-packed array.

31. The method of claim 29, wherein said fiber optic cables detect light from a limited defined region of the subject.

32. The method of claim 25, wherein said fluorescent protein is green fluorescent protein, lumazine, or yellow fluorescent protein.

33. The method of claim 25, wherein an input of light to excite the fluorescent protein is produced by a laser.

34. The method of claim 25, further comprising constructing a photon emission image from said measured photon emission.

35. The method of claim 10, further comprising acquiring a reflected light image of the subject, and superimposing said image of photon emission on said reflected light image to form a composite image.

36. The method of claim 25, wherein said expression of the heterologous gene is mediated by a constitutively active promoter.

37. The method of claim 25, wherein said expression of the heterologous gene is mediated by an inducible promoter.

38. The method of claim 37, wherein said inducible promoter is an interferon-inducible promoter.

39. The method of claim 37, wherein said inducible promoter is a promoter expressed in a disease state or a tissue-specific promoter.

40. The method of claim 39, wherein said disease state is inflammation.

41. The method of claim 40, wherein said promoter is E-selectin.

42. The method of claim 39, wherein said disease state is a tumor.

43. The method of claim 25, wherein expression of said heterologous gene is by a tumor cell.

44. The method of claim 25, further comprising:

repeating said detecting at selected intervals, wherein said repeating is effective to track localization of the expression of the heterologous gene in the subject over time.

45. The method of claim 25, further comprising administering a compound to said subject, and measuring photon emission from said subject after administration of said compound.

46. The method of claim 45, further comprising:

repeating at selected intervals said measuring after administration of said compound, wherein said repeating is effective to track an effect of said compound on a level of expression of said heterologous gene m said subject over time.

47. The method of claim 25, wherein said method further comprises, prior to said detecting, placing the subject in a detection field of the photodetector device.

48. The method of claim 25, wherein photons that make up said photon emission are visible light photons.

* * * * *